(12) United States Patent
Escary

(10) Patent No.: US 7,399,464 B2
(45) Date of Patent: Jul. 15, 2008

(54) POLYPEPTIDES OF THE IFNα-7 GENE

(75) Inventor: Jean-Louis Escary, Le Chesnay (FR)

(73) Assignee: GenOdyssee SA, Evry (FR)

( * ) Notice: Subject to any disclaimer, the term of this patent is extended or adjusted under 35 U.S.C. 154(b) by 492 days.

(21) Appl. No.: 10/732,485

(22) Filed: Dec. 11, 2003

(65) Prior Publication Data

US 2004/0126799 A1 Jul. 1, 2004

Related U.S. Application Data

(63) Continuation of application No. PCT/EP02/07456, filed on Jun. 11, 2002.

(30) Foreign Application Priority Data

Jun. 11, 2001 (FR) .................................. 01 07588

(51) Int. Cl.
*A61K 38/21* (2006.01)
*C07K 14/00* (2006.01)
*A01N 37/00* (2006.01)

(52) U.S. Cl. ........................... 424/85.7; 530/351; 514/2
(58) Field of Classification Search ........................ None
See application file for complete search history.

(56) References Cited

U.S. PATENT DOCUMENTS

| | | | |
|---|---|---|---|
| 4,678,751 A | 7/1987 | Goeddel | |
| 4,801,685 A | 1/1989 | Goeddel et al. | |
| 4,810,645 A | 3/1989 | Goeddel et al. | |
| 5,780,021 A | 7/1998 | Sobel | |
| 5,789,551 A | 8/1998 | Pestka | |
| 5,869,293 A | 2/1999 | Pestka | |
| 6,001,589 A | 12/1999 | Pestka | |
| 2004/0002474 A1* | 1/2004 | Heinrichs et al. | 514/44 |
| 2004/0105841 A1* | 6/2004 | Pestka | 424/85.4 |

FOREIGN PATENT DOCUMENTS

| | | |
|---|---|---|
| EP | 0072541 A2 | 2/1983 |
| EP | 0076489 A2 | 4/1983 |
| EP | 0088622 A2 | 9/1983 |
| GB | 2079291 | 1/1982 |
| GB | 2157697 | 10/1985 |
| GB | 2199830 | 7/1988 |
| JP | 57-158796 | 9/1982 |
| JP | 58-41849 | 3/1983 |
| JP | 60-227694 | 11/1985 |
| WO | WO 83/02457 | 7/1983 |
| WO | WO 83/02460 | 7/1983 |
| WO | WO 84/00776 | 3/1984 |
| WO | WO 86/06744 | 11/1986 |
| WO | WO 87/06613 | 11/1987 |
| WO | WO 00/39280 | 7/2000 |
| WO | WO 01/25438 A2 | 4/2001 |
| WO | WO 02/069913 A1 | 9/2002 |

OTHER PUBLICATIONS

Cohen S, et al. Cloning, expression and biological activity of a new variant of human intereron alpha identified in virus induced lymphoblastoid cells. Dev. Biol. Stand. 1985. vol. 60, p. 111-122.*
Mickle JE et al. Genotype-phenotype relationships in cystic fibrosis. Med. Clin. North Am. 2000. vol. 84, No. 3, pp. 597-607.*
International Search Report dated Jun. 13, 2003 for Application No. PCT/EP02/07456.
GenBank database, accession No. X02960: Human interferon alpha gene IFN-alpha 7.
O. I. Olopade et al., Mapping of the shortest region of overlap of deletions of the short arm of chromosome 9 associated with human neoplasia, Genomics, 14, pp. 437-443, (1992).
K. Henco et al., Structural relationship of human interferon alpha genes and pseudogenes, J. Mol. Biol. (1985) 185, pp. 227-260.
A. Ullrich et al., Nucleotide sequence of a portion of human chromosome 9 containing a leukocyte interferon gene cluster, J. Mol. Biol. (1982) 156, pp. 467-486.
M. Hussain et al., Identification of interferon-α14, and -α21 variants in the genome of a large human population, Journal of Interferon and Cytokine Research, 16 pp. 853-859 (1996).
H. Weber et al., Single amino acid changes that render human IFN-α2 biologically active on mouse cells, The EMBO Journal, vol. 6, No. 3, pp. 591-598, 1987.
A. Syvänen et al., Identification of individuals by analysis of biallelic DNA markers, using PCR and solid-phased minisequencing, Am. J. Hum. Genet., 52, pp. 46-59, 1993.
R. L. H. Jansen et al., Interleukin-2 interferon-α in the treatment of patients with advanced non-small-cell lung cancer, Journal of Immunotherapy, 12, pp. 70-73, 1992.
E. Mita et al., Predicting interferon therapy efficacy from hepatitis c virus genotype and RNA titer, Digestive Diseases and Sciences, vol. 39, No. 5 (May 1994), pp. 977-982.
R. Yamada et al., Identification of 142 single nucleotide polymorphisms in 41 candidate genes for rheumatoid arthritis in the Japanese population, Hum. Genet. (2000) 106, pp. 293-297.

* cited by examiner

*Primary Examiner*—Gary B. Nickol
*Assistant Examiner*—Bruce D. Hissong
(74) *Attorney, Agent, or Firm*—Hunton and Williams LLP

(57) ABSTRACT

The present invention relates to new polynucleotides derived from the nucleotide sequence of the IFNα-7 gene comprising new SNPs, and new polypeptides derived from the wild-type IFNα-7 protein comprising at least one mutation caused by at least one SNP of the invention as well as their therapeutic uses.

16 Claims, 7 Drawing Sheets

Figures 3, 3A, 3B:
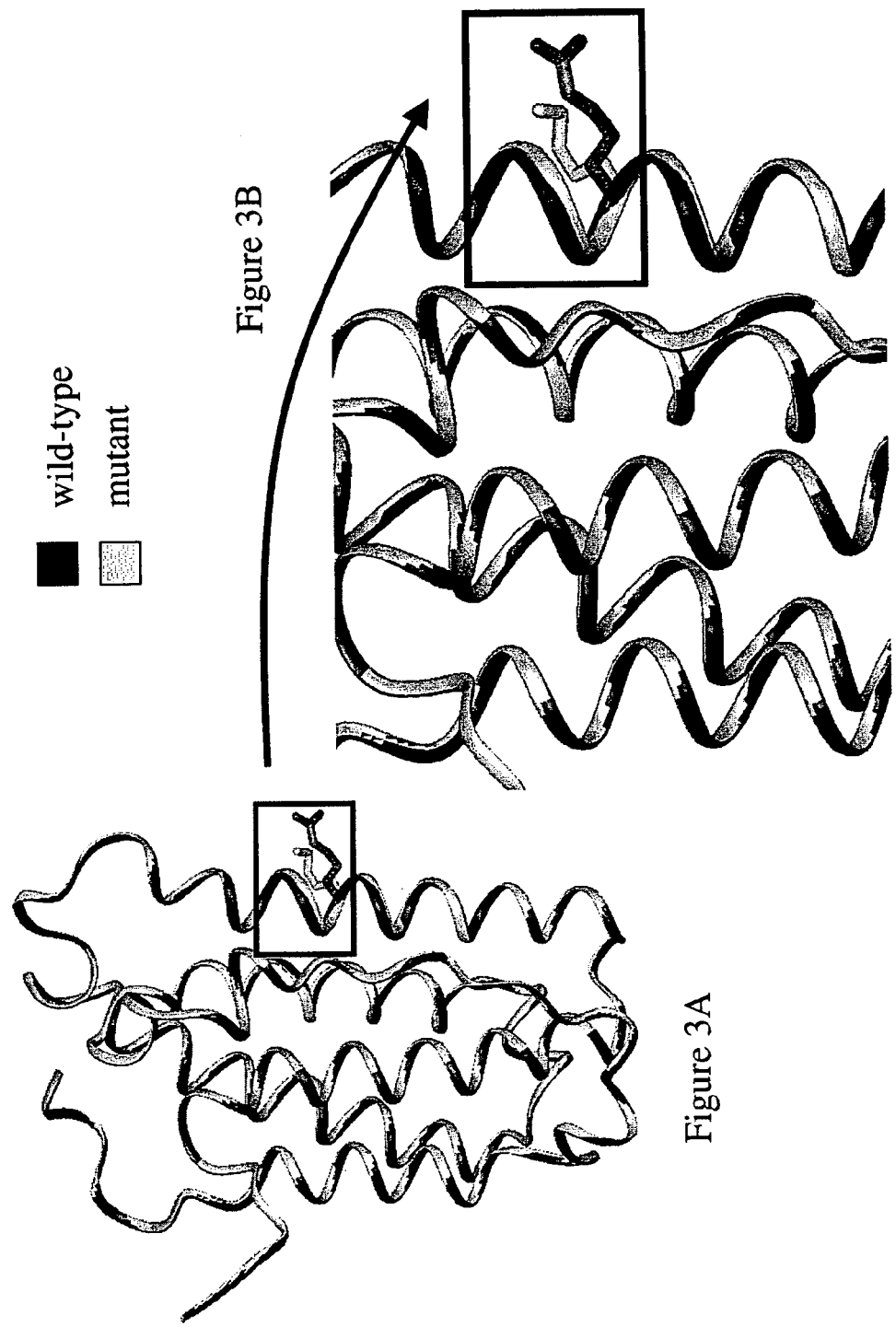

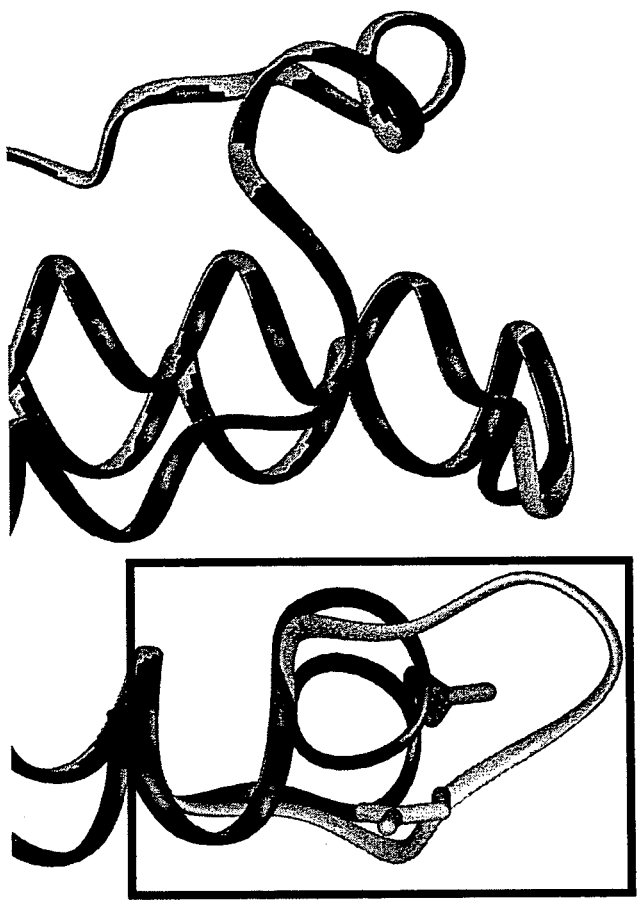
Figure 1
Figure 1A
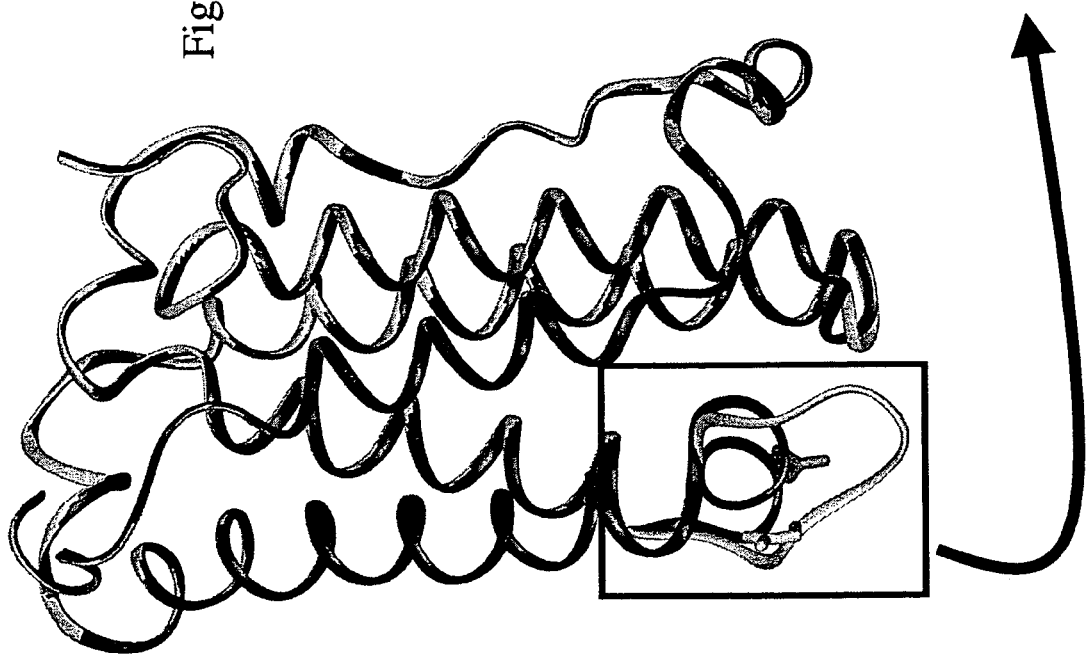
Figure 1B
■ wild-type
▨ mutant

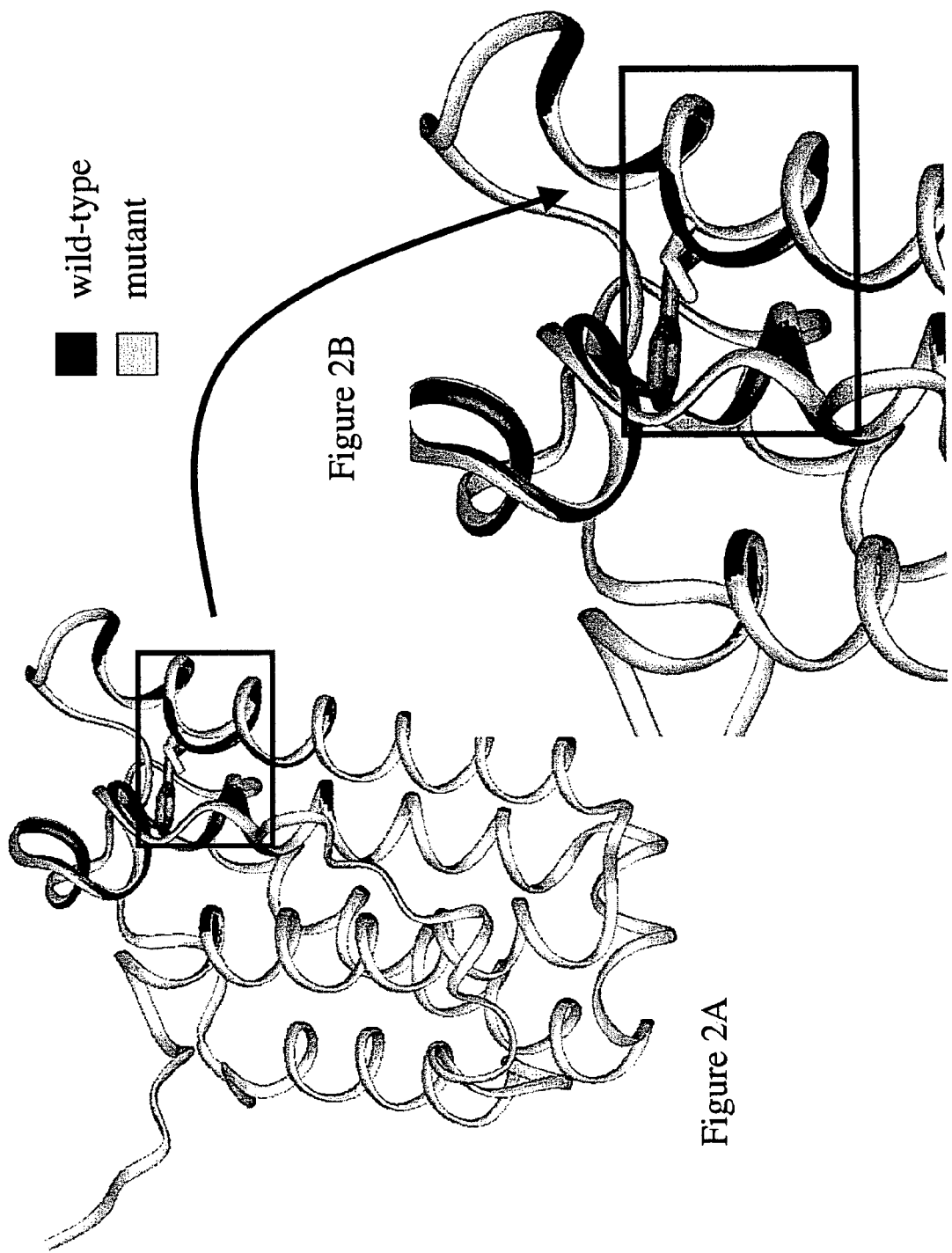

■ wild-type
▨ mutant

Figure 4
Figure 4A
Figure 4B

POLYPEPTIDES OF THE IFNα-7 GENE

CROSS-REFERENCE TO RELATED APPLICATIONS

This application is a continuation of PCT Application No. PCT/EP02/07456, filed Jun. 11, 2002, which claims the benefit of French Patent Application No. 01/07588, filed Jun. 11, 2001.

BACKGROUND OF THE INVENTION

1. Field of the Invention

The present invention relates to new polynucleotides derived from the nucleotide sequence of the IFNα-7 gene comprising new SNPs, and new polypeptides derived from the natural wild-type IFNα-7 protein comprising mutations caused by these SNPs, as well as their therapeutic uses.

2. Related Art

The interferon alpha 7 gene, hereinafter referred to as IFNα-7, is described in the following publications:

Olopade, O. I.; Bohlander, S. K.; Pomykala, H.; Maltepe, E.; Van Melle, E.; Le Beau, M. M.; Diaz, M. O.: "Mapping of the shortest region of overlap of deletions of the short arm of chromosome 9 associated with human neoplasia."; Genomics 14: 437-443, 1992.

Henco K, Brosius J, Fujisawa A, Fujisawa J I, Haynes J R, Hochstadt J, Kovacic T, Pasek M, Schambock A, Schmid J, et al.: "Structural relationship of human interferon alpha genes and pseudogenes."; J Mol Biol 1985 Sep. 20; 185(2): 227-60.

Ullrich A, Gray A, Goeddel D V, Dull T J: "Nucleotide sequence of a portion of human chromosome 9 containing a leukocyte interferon gene cluster."; J Mol. Biol. 1982 Apr. 15; 156(3): 467-86.

The nucleotide sequence of this gene is accessible under accession number X02960 in the GenBank database.

The IFNα are known for their cellular antiproliferative effects and their involvements in antiviral and antiparasitic responses.

The IFNα are also known to inhibit the expression of several other cytokines at the level of the hematopoietic stem cells, as well as to inhibit the cellular proliferation of certain tumors.

The IFNα are also known to reduce the expression of the receptors to the EGF in renal carcinomas, to inhibit the expression of certain mitochondrial genes, to inhibit the proliferation of fibroblasts, monocytes and B lymphocytes, especially in vitro, and to block the synthesis of antibodies by B lymphocytes.

The IFNα are also known to induce the expression of tumor specific antigens on the surface of tumor cells and also to induce the genes placed under the control of promoter regions of the ISRE type (Interferon-Stimulated Response Element) by acting on the specific transcription factors of these ISRE.

It is known that the IFNα are involved in different disorders and/or human diseases, such as the different cancers like for example, carcinomas, melanomas, lymphomas, leukemias and cancers of the liver, neck, head and kidneys, cardiovascular diseases, metabolic diseases such as those that are not connected with the immune system like, for example, obesity, infectious diseases such as hepatitis B and C and AIDS, pneumonias, ulcerative colitis, diseases of the central nervous system like, for example, Alzheimer's disease, schizophrenia and depression, the rejection of tissue or organ grafts, healing of wounds, anemia in dialyzed patients, allergies, asthma, multiple sclerosis, osteoporosis, psoriasis, rheumatoid arthritis, Crohn's disease, autoimmune diseases and disorders, gastrointestinal disorders or even disorders connected with chemotherapy treatments.

The IFNα are particularly used for the treatment of certain leukemias, metastasizing renal carcinomas as well as tumors that appear following an immunodeficiency, such as Kaposi's sarcoma in the case of AIDS. The IFNα are also effective against other types of tumors and against certain viral infections. The IFNα are also recognized by the FDA (Food and Drug Administration) for the treatment of genital warts or venereal diseases.

However, the IFNα, and in particular INFα-7, have numerous side effects when they are used in pharmaceutical compositions, such as reactions of acute hypersensitivity (urticaria, bronchoconstriction, anaphylactic shock etc.), cardiac arrythmias, low blood pressure, epileptic seizures, problems with thyroid functions, flu-like syndromes (fevers, sweats, myalgias), etc.

Furthermore, the patients treated with IFNα can develop antibodies neutralizing these molecules, thus decreasing their effectiveness.

The inventors have found new polypeptide and new polynucleotide analogs to the IFNα-7 gene capable of having a different functionality from the natural wild-type IFNα-7 protein.

These new polypeptides and polynucleotides can notably be used to treat or prevent the disorders or diseases previously mentioned and avoid all or part of the disadvantages, which are tied to them.

BRIEF SUMMARY OF THE INVENTION

The invention has as its first object new polynucleotides that differ from the nucleotide sequence of the reference wild-type INFα-7 gene, in that they comprise one or several SNPs (Single Nucleotide Polymorphism).

The nucleotide sequence SEQ ID NO. 1 of the human reference wild-type IFNα-7 gene is composed of 1983 nucleotides and comprises a coding sequence of 570 nucleotides, from nucleotide 751 (start codon) to nucleotide 1320 (stop codon).

The applicant has identified 14 SNPs in the nucleotide sequence of the reference wild-type INFα-7 gene. These 14 SNPs are the following: a559c, g580a, c667t, c682t, t779c, g1033a, c1084a, g1125a, g1135t, g1161a, t1166c, g1181a, a1212g, and a1294c.

It is understood, in the sense of the present invention, that the numbering corresponding to the positioning of the SNP previously defined is relative to the numbering of the nucleotide sequence SEQ ID NO. 1.

The letters a, t, c and g correspond respectively to the nitrogenous bases adenine, thymine, cytosine and guanine.

The first letter corresponds to the wild-type nucleotide, whereas the last letter corresponds to the mutated nucleotide.

Thus, for example, the SNP g1033a corresponds to a mutation of the nucleotide guanine (g) at position 1033 of the nucleotide sequence SEQ ID NO. 1 of the reference wild-type IFNα-7 gene, into nucleotide adenine (a).

These SNPs were identified by the applicant using the determination process described in applicant's patent application FR 00 22894, entitled "Process for the determination of one or several functional polymorphism(s) in the nucleotide sequence of a preselected functional candidate gene and its applications" and filed Dec. 6, 2000, cited here by way of reference.

The process described in this patent application permits the identification of one (or several) preexisting SNP(s) in at least one individual from a random population of individuals.

In the scope of the present invention, a fragment of the nucleotide sequence of the IFNα-7 gene, comprising, for example, the coding sequence, was isolated from different individuals in a population of individuals chosen in a random manner.

Sequencing of these fragments was then carried out on certain of these samples having a heteroduplex profile (that is a profile different from that of the reference wild-type INFα-7 gene sequence) after analysis by DHPLC ("Denaturing-High Performance Liquid Chromatography").

The fragment sequenced in this way was then compared to the nucleotide sequence of the fragment of the reference wild-type IFNα-7 gene and the SNPs in conformity with the invention identified.

Thus, the SNPs are natural and each of them is present in certain individuals of the world population.

The reference wild-type IFNα-7 gene codes for an immature protein of 189 amino acids, corresponding to the amino acid sequence SEQ ID NO. 2, that will be converted to a mature protein of 166 amino acids, by cleavage of the signal peptide that includes the first 23 amino acids.

Each of the coding SNPs of the invention, namely: t779c, g1033a, c1084a, g1135t, t1166c, g181a, a1294c, causes modifications, at the level of the amino acid sequence, of the protein encoded by the nucleotide sequence of the IFNα-7 gene.

These modifications in the amino acid sequence are the following:

The SNP t779c causes a mutation of the amino acid valine (V) at position 10 in the immature protein of the INFα-7 gene, corresponding to the amino acid sequence SEQ ID NO. 2, in alanine (A). This SNP affects an amino acid located in the signal sequence that will be cleaved during the process of protein maturation and, thus, this SNP is not found on the mature protein. In the description of the present invention, one will call V10A the mutation encoded by this SNP by reference to the immature protein.

The SNP g1033a causes a mutation of the amino acid aspartic acid (D) at position 95 in the immature protein of the IFNα-7 gene, corresponding to the amino acid sequence SEQ ID NO. 2, in asparagine (N) and at position 72 of the mature protein. In the description of the present invention, one will indifferently call D72N and D95N the mutation encoded by this SNP according to whether one refers respectively to the mature protein or to the immature protein.

The SNP c1084a causes a mutation of the amino acid leucine (L) at position 112 in the immature protein of the INFα-7 gene, corresponding to the amino acid sequence SEQ ID NO. 2, in isoleucine (I) and at position 89 of the mature protein. In the description of the present invention, one will indifferently call L89I and L112I the mutation encoded by this SNP according to whether one refers respectively to the mature protein or to the immature protein.

The SNP g1135t causes a mutation of the amino acid valine (V) at position 129 in the immature protein of the IFNα-7 gene, corresponding to the amino acid sequence SEQ ID NO. 2, in leucine (L) and at position 106 of the mature protein. In the description of the present invention, one will indifferently call V106L and V129L the mutation encoded by this SNP according to whether one refers respectively to the mature protein or to the immature protein.

The SNP t1166c causes a mutation of the amino acid phenylalanine (F) at position 139 in the immature protein of the IFNα-7 gene, corresponding to the amino acid sequence SEQ ID NO. 2, in serine (S) and at position 116 of the mature protein. In the description of the present invention, one will indifferently call F116S and F139S the mutation encoded by this SNP according to whether one refers respectively to the mature protein or to the immature protein.

The SNP g1181a causes a mutation of the amino acid arginine (R) at position 144 in the immature protein of the INFα-7 gene, corresponding to the amino acid sequence SEQ ID NO. 2, in lysine (K) and at position 121 of the mature protein. In the description of the present invention, one will indifferently call R121K and R144K the mutation encoded by this SNP according to whether one refers respectively to the mature protein or to the immature protein.

The SNP a1294c causes a mutation of the amino acid lysine (K) at position 182 in the immature protein of the IFNα-7 gene, corresponding to the amino acid sequence SEQ ID NO. 2, in glutamine (Q) and at position 159 of the mature protein. In the description of the present invention, one will indifferently call K159Q and K182Q the mutation encoded by this SNP according to whether one refers respectively to the mature protein or to the immature protein.

The SNPs g1033a (D95N), t1166c (F139S), g1181a (R144K), a1294c (K182Q), cause modifications of the spatial conformation of the polypeptides in conformity with the invention compared to the polypeptide encoded by the nucleotide sequence of the wild-type reference IFNα-7 gene.

These modifications can be observed by computational molecular modeling, according to methods that are well known to a person skilled in the art, making use of, for example, the modeling tools fold recognition (for example, SEQFOLD/MSI), homology (for example, MODELER/MSI), electrostatic fields (DELPHI/MSI), and/or molecular simulation (using force field to determine minimum energy conformations as well as dynamic trajectories of molecular systems, for example DISCOVER/MSI).

Examples of such models are given hereinafter in the experimental section.

Computational molecular modeling shows that the mutation D72N on the mature mutated protein causes a structural modification of the short helix (T70-A75) carrying the aspartic acid of position 72. The loop between helices D and E having the tyrosine residue at position 136, facing the aspartic acid of position 72, is also modified.

Thus, the mutated protein possesses a three-dimensional conformation different from the natural wild-type INFα-7 protein.

Moreover, the mutation D72N also causes the loss of the negative charge carried by the aspartic acid. Finally, the mutation of the aspartic acid residue of position 72 into an asparagine residue, in the vicinity of the INFα-7 part that binds to its receptor, must alter the protein function.

Therefore, computational molecular modeling predicts that the presence of the asparagine at position 72 involves a significant modification of the structure and of the function of the natural wild-type IFNα-7 protein. In particular, it is likely that this mutation changes the affinity of the INFα-7 protein to its receptor.

Computational molecular modeling shows that the mutation F116S on the mature mutated protein causes a slight perturbation of helix D but also a structural modification of the AB-loop at the level of the short helix (E40-D44). The orientation of the glutamate of position 42 located in this short helix is modified due to the mutation.

The most important effect of the F116S mutation is a weakening of the pi-staking effect caused by the network of phenylalanines in the inside of the IFNα-7 structure, which probably causes a higher flexibility in the protein structure.

The hydrogen bond between the nitrogen atom of the phenylalanine peptidic skeleton of position 116 with the oxygen atom of the glutamate carbonyl group of position 114 is conserved.

Thus, the mutated protein possesses a three-dimensional conformation different from the natural wild-type INFα-7 protein.

Therefore, computational molecular modeling predicts that the presence of the serine at position 116 involves a significant modification of the structure and of the function of the natural wild-type IFNα-7 protein.

Computational molecular modeling shows that the R121K mutation on the mature mutated protein causes a slight perturbation of helix D conformation.

The orientation of the side chains of the amino acids L118, K122, Q125 and F124 is modified by the mutation.

Moreover, it has been demonstrated that the R121 residue of IFNα-2 (equivalent to R120 in the IFNα-7 sequence) may be important for the antiviral activity of interferons (Weber H, Valenzuela D, Lujber G, Gubler M, Weissmann C.; "Single amino acid changes that render human IFN alpha 2 biologically active on mouse cells". (1987) EMBO J. 6: 591-598.).

Thus, the mutated protein possesses a three-dimensional conformation different from the natural wild-type IFNα-7 protein.

Therefore, computational molecular modeling predicts that the presence of the lysine at position 121 involves a significant modification of the structure and of the function of the natural wild-type IFNα-7 protein.

Computational molecular modeling shows that the K159Q mutation on the mature mutated protein causes a disturbance in the loop located after helix E, which effect probably continues till the C-terminal end of the protein. The loop located just before helix B is also modified at the level of the Q149 residue.

The hydrogen bridge between the nitrogen atom of lysine 159 and the oxygen atom of the carbonyl group of threonine 156 (end of helix E with C-terminal loop) is suppressed.

It is believed that the lysine (K) at position 159 may affect the antiviral activity of the interferons C-terminal part (Chang N T, Kung H F, Pestka S.; "Synthesis of a human leukocyte interferon with a modified carboxy terminus in *Escherichia coli.*" Arch. Biochem. Biophys. (1983) 221: 585-589).

Thus, the mutated protein possesses a three-dimensional conformation different from the natural wild-type IFNα-7 protein.

Therefore, computational molecular modeling predicts that the presence of the glutamine at position 159 involves a significant modification of the structure and of the function of the natural wild-type IFNα-7 protein.

Other SNPs in conformity with the invention, namely: a559c, g580a, c667t, c682t, g1125a, g1161a, and a1212g, do not involve modification of the protein encoded by the nucleotide sequence of the INFα-7 gene at the level of the amino acid sequence SEQ ID NO. 2.

The SNPs g1125a, g1161a, a1212g, are silent and the SNPs a559c, g580a, c667t, c682t, are non-coding.

Indeed, the silent SNP g1125a does not modify the amino acid glutamine (Q) at position 125 on the amino acid sequence SEQ ID NO. 2. The silent SNP g1161a does not modify the amino acid glutamic acid (E) at position 137 on the amino acid sequence SEQ ID NO. 2. Similarly, the silent SNP a1212g does not modify the amino acid leucine (L) at position 154 on the amino acid sequence SEQ ID NO. 2.

Genotyping of the polynucleotides in conformity with the invention can be carried out in such a fashion as to determine the allelic frequency of these polynucleotides in a population. Examples of genotyping are given, hereinafter, in the experimental section.

The determination of the functionality of the polypeptides of the invention can equally be carried out by a test of their biological activity.

In this regard, it is possible to measure, for example, signal transduction, dendritic cell maturation, cytokine release by CD4+ or CD8+ T-lymphocytes, cytokine release by monocytes, in vitro or in vivo antiviral activity, anti-tumoral activity in mice previously inoculated with malignant Friend erythroleukemia cells, cellular antiproliferative activity on Daudi Burkitt's cell line, cellular antiproliferative activity on TF-1 cell line of polypeptides in conformity with the invention and compare with the wild-type IFNα-7, or the wild-type IFNα-2 chosen as a representative of a commercial product.

The invention also has for an object the use of polynucleotides and of polypeptides in conformity with the invention as well as of therapeutic molecules obtained and/or identified starting from these polynucleotides and polypeptides, notably for the prevention and the treatment of certain human disorders and/or diseases.

BRIEF DESCRIPTION OF THE DRAWINGS

FIG. 1A represents a model of the encoded protein according to the invention comprising the SNP D72N and the natural wild-type IFNα-7 protein. FIG. 1B represents a close up of the model of the inferior part of each one of the proteins represented in FIG. 1A.

In FIGS. 1A and 1B, the black ribbon represents the structure of the natural wild-type INFα-7 protein and the white ribbon represents the structure of the D72N mutated INFα-7 protein.

FIG. 2A represents a model of the encoded protein according to the invention comprising the SNP F116S and the natural wild-type INFα-7 protein. FIG. 2B represents a close up of the model of the superior part of each of the proteins represented in FIG. 2A.

In FIGS. 2A and 2B, the black ribbon represents the structure of the natural wild-type IFNα-7 protein and the white ribbon represents the structure of the F116S mutated INFα-7 protein.

FIG. 3A represents a model of the encoded protein according to the invention comprising the SNP R121K and the natural wild-type INFα-7 protein. FIG. 3B represents a close up of the model of the central part of each of the proteins represented in FIG. 3A.

In FIGS. 3A and 3B, the black ribbon represents the structure of the natural wild-type INFα-7 protein and the white ribbon represents the structure of the R121K mutated INFα-7 protein.

FIG. 4A represents a model of the encoded protein according to the invention comprising the SNP K159Q and the natural wild-type INFα-7 protein. FIG. 4B represents a close up of the model of the superior part of each of the proteins represented in FIG. 4A.

In FIGS. 4A and 4B, the black ribbon represents the structure of the natural wild-type INFα-7 protein and the white ribbon represents the structure of the K159Q mutated INFα-7 protein.

FIG. 5 represents the results of the test for measuring the antiproliferative effect of D72N mutated INFα-7, on the TF-1 cell line. In this figure, the abscissas correspond to the concentration of IFNα (ng/mL) and the ordinates correspond to the inhibition of cell proliferation (%). The antiproliferative effect of the D72N mutated IFNα-7 (black diamonds) is compared to that of wild-type IFNα-2 (white squares).

Figure 6:
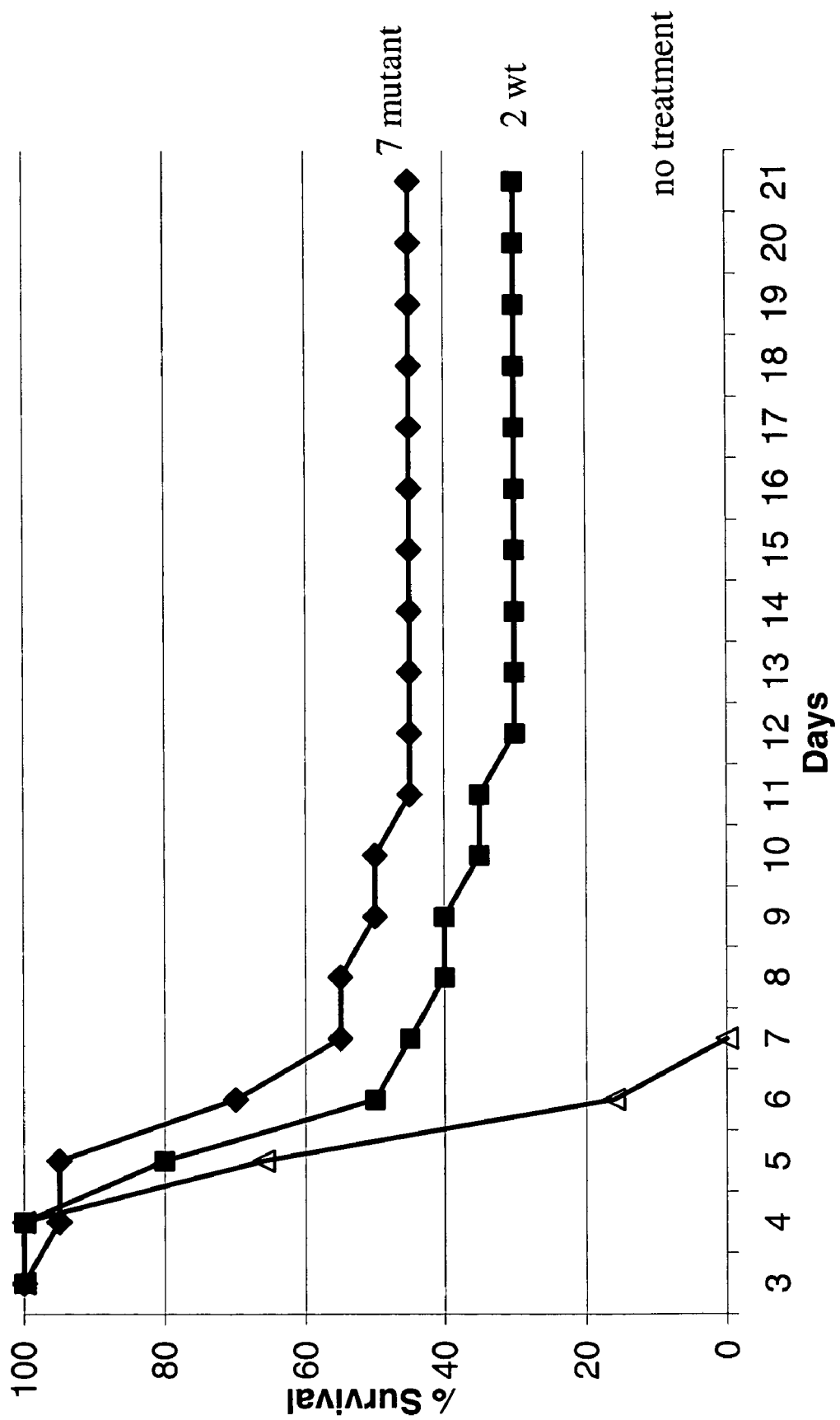
Figure 7:
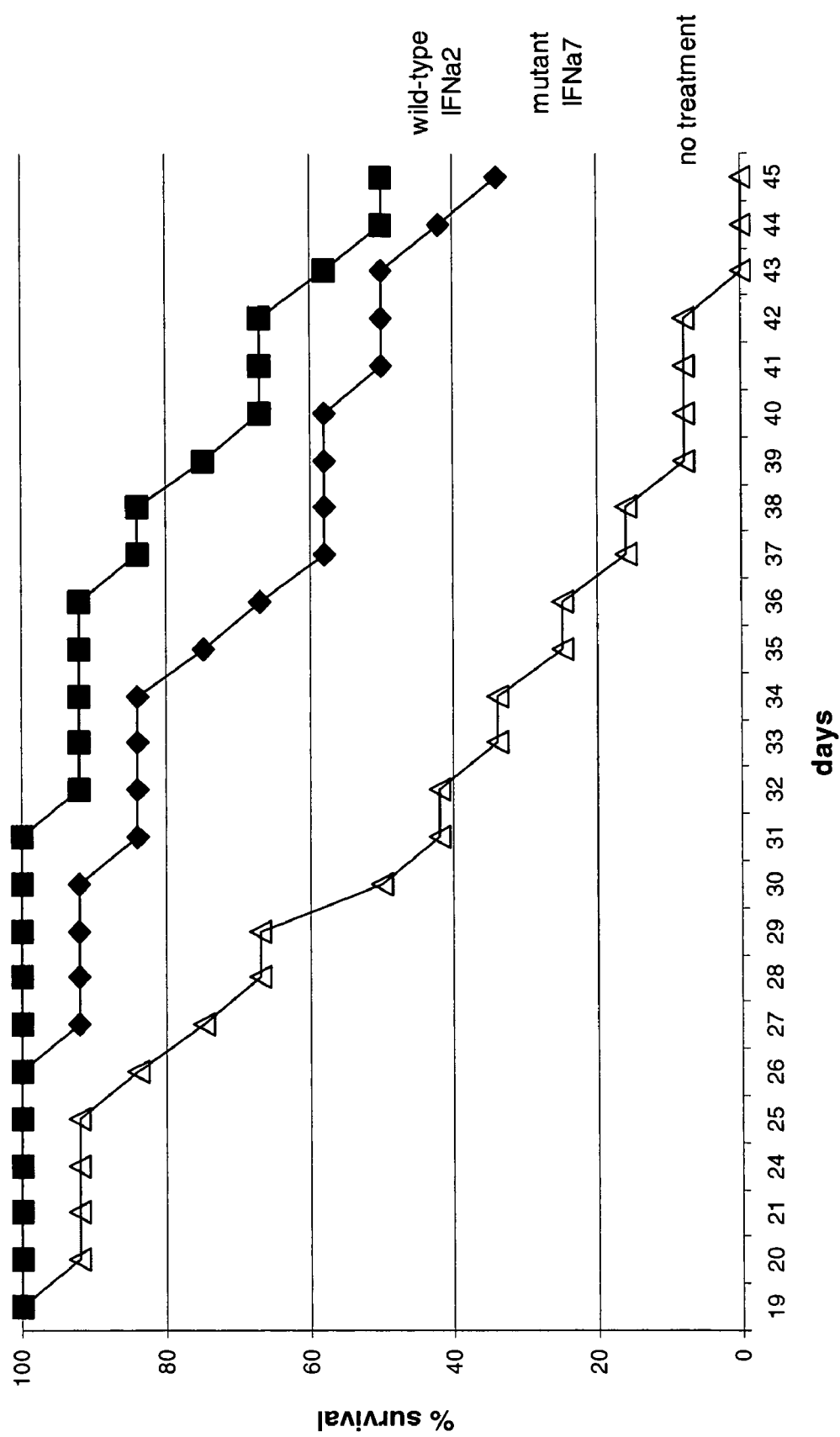

FIG. 6 represents the survival rate of mice previously infected by VSV virus and treated with D72N mutated IFNα-7 protein, in comparison to those treated with wild-type IFNα-2, or those which have not been treated. In this figure, the abscissas correspond to the time of survival (days) and the ordinates correspond to the relative survival rate of VSV infected mice. The black diamonds represent the data for VSV infected mice treated with D72N mutated INFα-7. The black squares represent the data for VSV infected mice treated with wild-type IFNα-2, and the open triangles represent the data for VSV infected mice which have not been treated.

FIG. 7 represents the survival rate of mice previously inoculated with malignant Friend erythroleukemia cells (FLC) and treated with D72N mutated IFNα-7 protein, in comparison to those treated with wild-type IFNα-2, or those which have not been treated. In this figure, the abscissas correspond to the time of survival (days) and the ordinates correspond to the relative survival rate of FLC inoculated mice. The black diamonds represent the data for FLC inoculated mice treated with. D72N mutated IFNα-7. The black squares represent the data for FLC inoculated mice treated with wild-type INFα-2, and the open triangles represent the data for FLC inoculated mice which have not been treated.

DETAILED DESCRIPTION OF THE INVENTION

Definitions

"Nucleotide sequence of the reference wild-type gene" is understood as the nucleotide sequence SEQ ID NO. 1 of the human IFNα-7 gene.

This sequence is accessible in GenBank under accession number X02960 and it is described in the following publications:

Olopade, O. I.; Bohlander, S. K.; Pomykala, H.; Maltepe, E.; Van Melle, E.; Le Beau, M. M.; Diaz, M. O.: "Mapping of the shortest region of overlap of deletions of the short arm of chromosome 9 associated with human neoplasia."; Genomics 14: 437-443, 1992.

Henco K, Brosius J, Fujisawa A, Fujisawa J I, Haynes J R, Hochstadt J, Kovacic T, Pasek M, Schambock A, Schmid J, et al.: "Structural relationship of human interferon alpha genes and pseudogenes."; J Mol Biol 1985 Sep. 20; 185(2): 227-60.

Ullrich A, Gray A, Goeddel D V, Dull T J: "Nucleotide sequence of a portion of human chromosome 9 containing a leukocyte interferon gene cluster."; J Mol. Biol. 1982 Apr. 15; 156(3): 467-86.

"Natural wild-type IFNα-7 protein" or "wild-type IFNα-7 protein" are understood as the mature protein encoded by the nucleotide sequence of the reference wild-type IFNα-7 gene. The natural wild-type immature protein IFNα-7 corresponds to the peptide sequence shown in SEQ ID NO. 2.

"Polynucleotide" is understood as a polyribonucleotide or a polydeoxyribonucleotide that can be a modified or non-modified DNA or an RNA.

The term polynucleotide includes, for example, a single strand or double strand DNA, a DNA composed of a mixture of one or several single strand region(s) and of one or several double strand region(s), a single strand or double strand RNA and an RNA composed of a mixture of one or several single strand region(s) and of one or several double strand region(s). The term polynucleotide can also include an RNA and/or a DNA including one or several triple strand regions. By polynucleotide is equally understood the DNAs and RNAs containing one or several bases modified in such a fashion as to have a skeleton modified for reasons of stability or for other reasons. By modified base is understood, for example, the unusual bases such as inosine.

"Polypeptide" is understood as a peptide, an oligopeptide, an oligomer or a protein comprising at least two amino acids joined to each other by a normal or modified peptide bond, such as in the cases of the isosteric peptides, for example.

A polypeptide can be composed of amino acids other than the 20 amino acids defined by the genetic code. A polypeptide can equally be composed of amino acids modified by natural processes, such as post translational maturation processes or by chemical processes, which are well known to a person skilled in the art. Such modifications are fully detailed in the literature. These modifications can appear anywhere in the polypeptide: in the peptide skeleton, in the amino acid chain or even at the carboxy- or amino-terminal ends.

A polypeptide can be branched following an ubiquitination or be cyclic with or without branching. This type of modification can be the result of natural or synthetic post-translational processes that are well known to a person skilled in the art.

For example, polypeptide modifications is understood to include acetylation, acylation, ADP-ribosylation, amidation, covalent fixation of flavine, covalent fixation of heme, covalent fixation of a nucleotide or of a nucleotide derivative, covalent fixation of a lipid or of a lipidic derivative, the covalent fixation of a phosphatidylinositol, covalent or non-covalent cross-linking, cyclization, disulfide bond formation, demethylation, cysteine formation, pyroglutamate formation, formylation, gamma-carboxylation, glycosylation, PEGylation, GPI anchor formation, hydroxylation, iodization, methylation, myristoylation, oxidation, proteolytic processes, phosphorylation, prenylation, racemization, seneloylation, sulfatation, amino acid addition such as arginylation or ubiquitination. Such modifications are fully detailed in the literature: PROTEINS-STRUCTURE AND MOLECULAR PROPERTIES, 2nd Ed., T. E. Creighton, New York, 1993, POST-TRANSLATIONAL COVALENT MODIFICATION OF PROTEINS, B. C. Johnson, Ed., Academic Press, New York, 1983, Seifter et al. "Analysis for protein modifications and nonprotein cofactors", Meth. Enzymol. (1990) 182: 626-646, and Rattan et al. "Protein Synthesis: Post-translational Modifications and Aging", Ann NY Acad Sci (1992) 663: 48-62.

"Isolated polynucleotide" or "isolated polypeptide" are understood as a polynucleotide or a polypeptide respectively such as previously defined which is isolated from the human body or otherwise produced by a technical process.

"Identity" is understood as the measurement of nucleotide or polypeptide sequence identity.

Identity is a term well known to a person skilled in the art and well described in the literature. See COMPUTATIONAL MOLECULAR BIOLOGY, Lesk, A. M., Ed., Oxford University Press, New York, 1998; BIOCOMPUTING INFORMATICS AND GENOME PROJECT, Smith, D. W., Ed., Academic Press, New York, 1993; COMPUTER ANALYSIS OF SEQUENCE DATA, PART I, Griffin, A. M. and Griffin H. G., Ed, Humana Press, New Jersey, 1994; and SEQUENCE ANALYSIS IN MOLECULAR BIOLOGY, von Heinje, G., Academic Press, 1987.

The methods commonly employed to determine the identity and the similarity between two sequences are equally well described in the literature. See GUIDE TO HUGE COM- PUTER, Martin J. Bishop, Ed, Academic Press, San Diego, 1994, and Carillo H. and Lipton D., Siam J Applied Math (1988) 48: 1073.

A polynucleotide having, for example, an identity of at least 95% with the nucleotide sequence SEQ ID NO. 1 is a polynucleotide which contains at most 5 points of mutation over 100 nucleotides, compared to said sequence.

These points of mutation can be one (or several) substitution(s), addition(s) and/or deletion(s) of one (or several) nucleotide(s).

In the same way, a polypeptide having, for example, an identity of at least 95% with the amino acid sequence SEQ ID NO. 2 is a polypeptide that contains at most 5 points of mutation over 100 amino acids, compared to said sequence.

These points of mutation can be one (or several) substitution(s), addition(s) and/or deletion(s) of one (or several) amino acid(s).

The polynucleotides and the polypeptides according to the invention which are not totally identical with respectively the nucleotide sequence SEQ ID NO. 1 or the amino acid sequence SEQ ID NO. 2, it being understood that these sequences contains at least one of the SNPs of the invention, are considered as variants of these sequences.

Usually a polynucleotide according to the invention possesses the same or practically the same biological activity as the nucleotide sequence SEQ ID NO. 1 comprising at least one of the SNPs of the invention.

In similar fashion, usually a polypeptide according to the invention possesses the same or practically the same biological activity as the amino acid sequence SEQ ID NO. 2 comprising at least one of the coding SNPs of the invention.

A variant, according to the invention, can be obtained, for example, by site-directed mutagenesis or by direct synthesis.

By "SNP" is understood any natural variation of a base in a nucleotide sequence. A SNP, on a nucleotide sequence, can be coding, silent or non-coding.

A coding SNP is a polymorphism included in the coding sequence of a nucleotide sequence that involves a modification of an amino acid in the sequence of amino acids encoded by this nucleotide sequence. In this case, the term SNP applies equally, by extension, to a mutation in an amino acid sequence.

A silent SNP is a polymorphism included in the coding sequence of a nucleotide sequence that does not involve a modification of an amino acid in the amino acid sequence encoded by this nucleotide sequence.

A non-coding SNP is a polymorphism included in the non-coding sequence of a nucleotide sequence. This polymorphism can notably be found in an intron, a splicing zone, a transcription promoter or a site enhancer sequence.

By "functional SNP" is understood a SNP, such as previously defined, which is included in a nucleotide sequence or an amino acid sequence, having a functionality.

By "functionality" is understood the biological activity of a polypeptide or of a polynucleotide.

The functionality of a polypeptide or of a polynucleotide according to the invention can consist in a conservation, an augmentation, a reduction or a suppression of the biological activity of the polypeptide encoded by the nucleotide sequence of the wild-type reference gene or of this latter nucleotide sequence.

The functionality of a polypeptide or of a polynucleotide according to the invention can equally consist in a change in the nature of the biological activity of the polypeptide encoded by the nucleotide sequence of the reference wild-type gene or of this latter nucleotide sequence.

The biological activity can, notably, be linked to the affinity or to the absence of affinity of a polypeptide according to the invention with a receptor.

Polynucleotide

The present invention has for its first object an isolated polynucleotide comprising:
  a) a nucleotide sequence having at least 80% identity, preferably at least 90% identity, more preferably at least 95% identity and still more preferably at least 99% identity with the sequence SEQ ID NO. 1 or its coding sequence (from nucleotide 751 to nucleotide 1320), it being understood that this nucleotide sequence comprises at least one of the following coding SNPs t779c, g1033a, c1084a, g1135t, t1166c, g1181a, a1294c, or
  b) a nucleotide sequence complementary to a nucleotide sequence under a).

It is understood, in the sense of the present invention, that the numbering corresponds to the positioning of the SNPs in the nucleotide sequence SEQ ID NO. 1.

The present invention relates equally to an isolated polynucleotide comprising:
  a) a nucleotide sequence SEQ ID NO. 1 or its coding sequence, it being understood that each of these sequences comprises at least one of the following coding SNPs: t779c, g1033a, c1084a, g1135t, t1166c, g1181a, a1294c; or
  b) a nucleotide sequence complementary to a nucleotide sequence under a).

Preferably, the polynucleotide of the invention consists of the sequence SEQ ID NO. 1 or its coding sequence, it being understood that each of these sequences comprises at least one of the following coding SNPs: t779c, g1033a, c1084a, g1135t, t1166c, g1181a, a1294c.

According to the invention, the polynucleotide previously defined comprises a single coding SNP selected from the group consisting of: t779c, g1033a, c1084a, g1135t, t1166c, g1181a, and a1294c.

More preferably, the polynucleotide previously defined comprises the coding SNP g1033a.

A polynucleotide such as previously defined can equally include at least one of the following non-coding and silent SNPs: a559c, g580a, c667t, c682t, g1125a, g1161a, and a1212g.

The present invention equally has for its object an isolated polynucleotide comprising or consisting of:
  a) a nucleotide sequence SEQ ID NO. 1 or if necessary its coding sequence, it being understood that each of these sequences comprises at least one of the following non coding or silent SNPs: a559c, g580a, c667t, c682t, g1125a, g1161a, and a1212g; or
  b) a nucleotide sequence complementary to a nucleotide sequence under a).

It is well understood that only the following silent SNPs g1125a, g1161a, a1212g, are located in the coding sequence of the nucleotide sequence SEQ ID NO. 1.

The present invention also concerns an isolated polynucleotide consisting of a part of:
  a) a nucleotide sequence SEQ ID NO. 1 or its coding sequence, it being understood that each of these sequences comprises at least one of the following SNPs: a559c, g580a, c667t, c682t, t779c, g1033a, c1084a, g1125a, g1135t, g1161a, t1166c, g1181a, a1212g, and a1294c, or
  b) a nucleotide sequence complementary to a nucleotide sequence under a).

said isolated polynucleotide being composed of at least 10 nucleotides.

Preferably, the isolated polynucleotide as defined above is composed of 10 to 40 nucleotides.

The present invention also concerns an isolated polynucleotide comprising:
a) all or part of the nucleotide sequence SEQ ID NO. 1, provided that such nucleotide sequence, or part of sequence, comprises at least one SNP selected from the group consisting of a559c, g580a, c667t, c682t, t779c, g1033a, c1084a, g1125a, g1135t, g1161a, t1166c, g1181a, and a1212g; or
b) a nucleotide sequence complementary to a nucleotide sequence under a).

The isolated polynucleotide as defined above is composed of at least 10 nucleotides, and preferably from 10 to 40 nucleotides.

According to the invention, the polynucleotide previously defined comprises a single coding SNP selected from the group consisting of: t779c, g1033a, c1084a, g1135t, t1166c, g1181a, and a1294c.

More preferably, the polynucleotide previously defined comprises the coding SNP g1033a.

The present invention also has for its object an isolated polynucleotide coding for a polypeptide comprising all or part of:
a) the amino acid sequence SEQ ID NO. 2; or
b) the amino acid sequence comprising the amino acids included between positions 24 and 189 in the sequence of amino acids SEQ ID NO. 2;

it being understood that said polypeptide has an amino acid sequence comprising at least one of the following coding SNPs: V10A, D95N, L112I, V129L, F139S, R144K, and K182Q.

It is understood, in the sense of the present invention, that the numbering corresponding to the positioning of the V10A, D95N, L121I, V129L, F139S, R144K, and K182Q SNPs is relative to the numbering of the amino acid sequence SEQ ID NO. 2.

According to a preferred object of the invention, the previously defined polypeptide comprises a single coding SNP such as defined above.

More preferably, an isolated polynucleotide according to the invention codes for a polypeptide comprising all or part of the amino acid sequence SEQ ID NO. 2 and having the coding SNP D95N.

Preferably a polynucleotide according to the invention is composed of a DNA or RNA molecule.

A polynucleotide according to the invention can be obtained by standard DNA or RNA synthetic methods.

A polynucleotide according to the invention can equally be obtained by site-directed mutagenesis starting from the nucleotide sequence of the IFNα-7 gene by modifying the wild-type nucleotide by the mutated nucleotide for each SNP on the nucleotide sequence SEQ ID NO. 1.

For example, a polynucleotide according to the invention, comprising SNP g1033a can be obtained by site-directed mutagenesis starting from the nucleotide sequence of the INFα-7 gene by modifying the nucleotide guanine by the nucleotide adenine at position 1033 on the nucleotide sequence SEQ ID NO. 1.

The processes of site-directed mutagenesis that can be implemented in this way are well known to a person skilled in the art. The publication of T A Kunkel in 1985 in "Proc. Natl. Acad. Sci. USA" 82:488 can notably be mentioned.

An isolated polynucleotide can equally include, for example, nucleotide sequences coding for pre-, pro- or pre-pro-protein amino acid sequences or marker amino acid sequences, such as hexa-histidine peptide.

A polynucleotide of the invention can equally be associated with nucleotide sequences coding for other proteins or protein fragments in order to obtain fusion proteins or other purification products.

A polynucleotide according to the invention can equally include nucleotide sequences such as the 5' and/or 3' non-coding sequences, such as, for example, transcribed or non-transcribed sequences, translated or non-translated sequences, splicing signal sequences, polyadenylated sequences, ribosome binding sequences or even sequences which stabilize mRNA.

A nucleotide sequence complementary to the nucleotide or polynucleotide sequence is defined as one that can hybridize with this nucleotide sequence, under stringent conditions.

"Stringent hybridization conditions" is generally but not necessarily understood as the chemical conditions that permit a hybridization when the nucleotide sequences have an identity of at least 80%, preferably greater than or equal to 90%, still more preferably greater than or equal to 95% and most preferably greater than or equal to 97%.

The stringent conditions can be obtained according to methods well known to a person skilled in the art and, for example, by an incubation of the polynucleotides, at 42° C., in a solution comprising 50% formamide, 5×SSC (150 mM of NaCl, 15 mM of trisodium citrate), 50 mM of sodium phosphate (pH=7.6), 5×Denhardt Solution, 10% dextran sulfate and 20 µg denatured salmon sperm DNA, followed by washing the filters at 0.1×SSC, at 65° C.

Within the scope of the invention, when the stringent hybridization conditions permit hybridization of the nucleotide sequences having an identity equal to 100%, the nucleotide sequence is considered to be strictly complementary to the nucleotide sequence such as described under a).

It is understood within the meaning of the present invention that the nucleotide sequence complementary to a nucleotide sequence comprises at least one anti-sense SNP according to the invention.

Thus, for example, if the nucleotide sequence comprises the SNP g1033a, its complementary nucleotide sequence comprises the nucleotide thymine (t) at the equivalent of position 1033.

Identification, Hybridization and/or Amplification of a Polynucleotide Comprising a SNP The present invention also has for its object the use of all or part of:
a) a polynucleotide having 80 to 100% identity (preferably at least 90% identity, more preferably 95% identity and particularly 100% identity) with the nucleotide sequence SEQ ID NO. 1, and/or
b) a polynucleotide according to the invention comprising at least one SNP in order to identify, hybridize and/or amplify all or part of a polynucleotide having 80 to 100% identity (preferably at least 90% identity, more preferably 95% identity and particularly 100% identity) with the nucleotide sequence SEQ ID NO. 1 or if necessary its coding sequence (from nucleotide 751 to nucleotide 1320), it being understood that each one of these sequences comprises at least one of the following SNPs: a559c, g580a, c667t, c682t, t779c, g1033a, c1084a, g1125a, g1135t, g1161a, t1166c, g1181a, a1212g, and a1294c.

The present invention also concerns a method for identifying or amplifying all or part of a polynucleotide having 80 to 100% identity with nucleotide sequence SEQ ID NO. 1 comprising hybridizing, under appropriate hybridization conditions, said polynucleotide with the polynucleotide according to the invention.

Genotyping and Determination of the Frequency of a SNP

The present invention equally has for its object the use of all or part of:
  a) a polynucleotide having 80 to 100% identity (preferably at least 90% identity, more preferably 95% identity and particularly 100% identity) with the nucleotide sequence SEQ ID NO. 1, and/or
  b) a polynucleotide according to the invention comprising at least one SNP for the genotyping of all or part of a polynucleotide having 80 to 100% identity (preferably at least 90% identity, more preferably 95% identity and particularly 100% identity) with the nucleotide sequence SEQ ID NO. 1 or if necessary its coding sequence (from nucleotide 751 to nucleotide 1320), it being understood that each one of these sequences comprises at least one of the following SNPs: a559c, g580a, c667t, c682t, t779c, g1033a, c1084a, g1125a, g1135t, g1161a, t1166c, g1181a, a1212g, and a1294c.

The present invention also concerns a method for genotyping all or part of a polynucleotide having 80 to 100% identity with nucleotide sequence SEQ ID NO. 1 comprising the steps of amplifying a region of interest in the genomic DNA of a subject or a population of subjects, and determining the allele of at least one position in the nucleotide sequence SEQ ID NO. 1 chosen from the group consisting of 559, 580, 667, 682, 779, 1033, 1084, 1125, 1135, 1161, 1166, 1181, and 1212.

According to the invention, the genotyping may be carried out on an individual or a population of individuals.

Within the meaning of the invention, genotyping is defined as a process for the determination of the genotype of an individual or of a population of individuals. Genotype consists of the alleles present at one or more specific loci.

"Population of individuals" is understood as a group of individuals selected in random or non-random fashion. These individuals can be humans, animals, microorganisms or plants.

Usually, the group of individuals comprises at least 10 individuals, preferably from 100 to 300 individuals.

The individuals can be selected according to their ethnicity or according to their phenotype, notably those who are affected by the following disorders and/or diseases: carcinomas, melanomas, lymphomas, leukemias and cancers of the liver, neck, head and kidneys, cardiovascular diseases, metabolic diseases such as those that are not connected with the immune system like, for example, obesity, infectious diseases in particular viral infections like hepatitis B and C and AIDS, pneumonias, ulcerative colitis, diseases of the central nervous system like, for example, Alzheimer's disease, schizophrenia and depression, the rejection of tissue or organ grafts, healing of wounds, anemia in dialyzed patients, allergies, asthma, multiple sclerosis, osteoporosis, psoriasis, rheumatoid arthritis, Crohn's disease, autoimmune diseases and disorders, gastrointestinal disorders or even disorders connected with chemotherapy treatments.

A functional SNP according to the invention is preferably genotyped in a population of individuals.

Multiple technologies exist which can be implemented in order to genotype SNPs (see notably Kwok Pharmacogenomics, 2000, vol 1, pp 95-100. "High-throughput genotyping assay approaches"). These technologies are based on one of the four following principles: allele specific oligonucleotide hybridization, oligonucleotide elongation by dideoxynucleotides optionally in the presence of deoxynucleotides, ligation of allele specific oligonucleotides or cleavage of allele specific oligonucleotides. Each one of these technologies can be coupled to a detection system such as measurement of direct or polarized fluorescence, or mass spectrometry.

Genotyping can notably be carried out by minisequencing with hot ddNTPs (2 different ddNTPs labeled by different fluorophores) and cold ddNTPs (2 different non labeled ddNTPs), in connection with a polarized fluorescence scanner. The minisequencing protocol with reading of polarized fluorescence (FP-TDI Technology or Fluorescence Polarization Template-direct Dye-Terminator Incorporation) is well known to a person skilled in the art.

It can be carried out on a product obtained after amplification by polymerase chain reaction (PCR) of the DNA of each individual. This PCR product is selected to cover the polynucleotide genic region containing the studied SNP. After the last step in the PCR thermocycler, the plate is then placed on a polarized fluorescence scanner for a reading of the labeled bases by using fluorophore specific excitation and emission filters. The intensity values of the labeled bases are reported on a graph.

For the PCR amplification, in the case of a SNP of the invention, the sense and antisense primers, respectively, can easily be selected by a person skilled in the art according to the position of the SNPs of the invention.

For example, the sense and antisense nucleotide sequences corresponding to the primers used for the PCR amplification of a nucleotide sequence comprising the INFα-7 coding sequence can be, respectively:

```
SEQ ID NO. 3:   Sense       TACCCACCTCAGGTAGCC
                primer:

SEQ ID NO. 4:   Antisense   CATGAAAGTGTGAGATGATGC
                primer:
```

These nucleotide sequences permit amplification of a fragment having a length of 669 nucleotides, from nucleotide 711 to nucleotide 1379 in the nucleotide sequence SEQ ID NO. 1.

A statistical analysis of the frequency of each allele (allelic frequency) encoded by the gene comprising the SNP in the population of individuals is then achieved, which permits determination of the importance of their impact and their distribution in the different sub-groups and notably, if necessary, the diverse ethnic groups that constitute this population of individuals.

The genotyping data are analyzed in order to estimate the distribution frequency of the different alleles observed in the studied populations. The calculations of the allelic frequencies can be carried out with the help of software such as SAS-suite® (SAS) or SPLUS® (MathSoft). The comparison of the allelic distributions of a SNP of the invention across different ethnic groups of the population of individuals can be carried out by means of the software ARLEQUIN® and SAS-suite®.

SNPs of the Invention as Genetic Markers

Whereas SNPs modifying functional sequences of genes (e.g. promoter, splicing sites, coding region) are likely to be directly related to disease susceptibility or resistance, all SNPs (functional or not) may provide valuable markers for the identification of one or several genes involved in these disease states and, consequently, may be indirectly related to these disease states (See Cargill et al. (1999). Nature Genetics 22:231-238; Riley et al. (2000). Pharmacogenomics 1:39-47; Roberts L. (2000). Science 287: 1898-1899).

Thus, the present invention also concerns a databank comprising at least one of the following SNPs: a559c, g580a, c667t, c682t, t779c, g1033a, c1084a, g1125a, g1135t, g1161a, t1166c, g1181a, a1212g, and a1294c, in a polynucleotide of the IFNα-7 gene.

It is well understood that said SNPs are numbered in accordance with the nucleotide sequence SEQ ID NO. 1.

This databank may be analyzed for determining statistically relevant associations between:
 (i) at least one of the following SNPs: a559c, g580a, c667t, c682t, t779c, g1033a, c1084a, g1125a, g1135t, g1161a, t1166c, g1181a, a1212g, and a1294c, in a polynucleotide of the IFNα-7 gene, and
 (ii) a disease or a resistance to a disease.

The present invention also concerns the use of at least one of the following SNPs: a559c, g580a, c667t, c682t, t779c, g1033a, c1084a, g1125a, g1135t, g1161a, t1166c, g1181a, a1212g, and a1294c, in a polynucleotide of the IFNα-7 gene, for developing diagnostic/prognostic kits for a disease or a resistance to a disease.

A SNP of the invention such as defined above may be directly or indirectly associated to a disease or a resistance to a disease.

Preferably, these diseases may be those which are defined as mentioned hereinafter.

The present invention concerns also a method for determining statistically relevant associations between at least one SNP selected from the group consisting of a559c, g580a, c667t, c682t, t779c, g1033a, c1084a, g1125a, g1135t, g1161a, t1166c, g1181a, a1212g, and a1294c, in the IFNα-7 gene, and a disease or resistance to disease comprising:
 a) Genotyping a group of individuals;
 b) Determining the distribution of said disease or resistance to disease within said group of individuals;
 c) Comparing the genotype data with the distribution of said disease or resistance to disease; and
 d) Analyzing said comparison for statistically relevant associations.

The present invention equally concerns a method for diagnosing or determining a prognosis of a disease or a resistance to a disease comprising detecting at least one SNP selected from the group consisting of a559c, g580a, c667t, c682t, t779c, g1033a, c1084a, g1125a, g1135t, g1161a, t1166c, g1181a, a1212g, and a1294c, in the IFNα-7 gene.

Detection of the SNPs of the invention may be carried out by methods well known to a person skilled in the art such as those described below.

The detection of at least one SNP of the invention may be carried out starting from biological samples from the subject to be studied, such as cells, blood, urine, saliva, or starting from a biopsy or an autopsy of the subject to be studied. The genomic DNA may be used for the detection directly or after a PCR amplification, for example. RNA or cDNA can equally be used in a similar fashion.

It is then possible to compare the nucleotide sequence of the polynucleotide isolated from the subject with the nucleotide sequence of a polynucleotide comprising at least one SNP of the invention.

The comparison of the nucleotide sequences can be carried out by sequencing, by DNA hybridization methods, by mobility difference of the DNA fragments on an electrophoresis gel with or without denaturing agents or by melting temperature difference. See Myers et al., Science (1985) 230: 1242. Such modifications in the structure of the nucleotide sequence at a precise point can equally be revealed by nuclease protection tests, such as RNase and the S1 nuclease or also by chemical cleaving agents. See Cotton et al., Proc. Nat. Acad. Sci. USA (1985) 85: 4397-4401. A combination of DNA hybridization methods and enzymatic digestion may also be used as in the Invader assay. Oligonucleotide probes comprising a polynucleotide fragment of the invention can equally be used to conduct the screening.

Expression Vector and Host Cells

The present invention also has for its object a recombinant vector comprising at least one polynucleotide according to the invention.

Numerous expression systems can be used, including without limitation chromosomes, episomes, and derived viruses. More particularly, the recombinant vectors used can be derived from bacterial plasmids, transposons, yeast episomes, insertion elements, yeast chromosome elements, viruses such as baculovirus, papilloma viruses such as SV40, vaccinia viruses, adenoviruses, fox pox viruses, pseudorabies viruses, retroviruses.

These recombinant vectors can equally be cosmid or phagemid derivatives. The nucleotide sequence can be inserted in the recombinant expression vector by methods well known to a person skilled in the art such as, for example, those that are described in MOLECULAR CLONING: A LABORATORY MANUAL, Sambrook et al., 4th Ed., Cold Spring Harbor Laboratory Press, Cold Spring Harbor, N.Y., 2001.

The recombinant vector can include nucleotide sequences that control the regulation of the polynucleotide expression as well as nucleotide sequences permitting the expression and the transcription of a polynucleotide of the invention and the translation of a polypeptide of the invention, these sequences being selected according to the host cells that are used.

Thus, for example, an appropriate secretion signal can be integrated in the recombinant vector so that the polypeptide, encoded by the polynucleotide of the invention, will be directed towards the lumen of the endoplasmic reticulum, towards the periplasmic space, on the membrane or towards the extracellular environment.

The present invention also has for its object a host cell comprising a recombinant vector according to the invention.

The introduction of the recombinant vector in a host cell can be carried out according to methods that are well known to a person skilled in the art such as those described in BASIC METHODS IN MOLECULAR BIOLOGY, Davis et al., 2nd ed., McGraw-Hill Professional Publishing, 1995, and MOLECULAR CLONING: A LABORATORY MANUAL, supra, such as transfection by calcium phosphate, transfection by DEAE dextran, transfection, microinjection, transfection by cationic lipids, electroporation, transduction or infection.

The host cell can be, for example, bacterial cells such as cells of streptococci, staphylococci, *E. coli* or *Bacillus subtilis*, cells of fungi such as yeast cells and cells of *Aspergillus*, *Streptomyces*, insect cells such as cells of *Drosophila* S2 and of *Spodoptera* Sf9, animal cells, such as CHO, COS, HeLa, C127, BHK, HEK 293 cells and human cells of the subject to treat or even plant cells.

The host cells can be used, for example, to express a polypeptide of the invention or as active product in pharmaceutical compositions, as will be seen hereinafter.

Polypeptide

The present invention also has for its object an isolated polypeptide comprising an amino acid sequence having at least 80% identity, preferably at least 90% identity, more preferably at least 95% identity and still more preferably at least 99% identity with all or part of:

a) the amino acid sequence SEQ ID NO. 2, or b) the amino acid sequence comprising the amino acids included between positions 24 and 189 of the amino acid sequence SEQ ID NO. 2, it being understood that said polypeptide contains at least one of the following coding SNPs: V10A, D95N, L121, V129L, F139S, R144K, K182Q.

The polypeptide of the invention can equally comprise all or part of:

a) the amino acid sequence SEQ ID NO. 2, or b) the amino acid sequence containing the amino acids included between positions 24 and 189 of the amino acid sequence SEQ ID NO. 2, it being understood that said polypeptide contains at least one of the following coding SNPs: V10A, D95N, L121, V129L, F139S, R144K, K182Q.

The polypeptide of the invention can more particularly consist of all or part of:

a) the amino acid sequence SEQ ID NO. 2, or b) the amino acid sequence containing the amino acids included between positions 24 and 189 of the amino acid sequence SEQ ID NO. 2, it being understood that said polypeptide contains at least one of the following coding SNPs: V10A, D95N, L121, V129L, F139S, R144K, K182Q.

Preferably, a polypeptide according to the invention contains a single coding SNP selected from the group consisting of: V10A, D95N, L112I, V129L, F139S, R144K, K182Q.

More preferably, the polypeptide according to the invention comprises amino acids 24 through 189 of the amino acid sequence SEQ ID NO. 2, and has the coding SNP D95N.

The present invention equally has for its object a process for the preparation of the above-described polypeptide, in which a previously defined host cell is cultivated in a culture medium and said polypeptide is isolated from the culture medium.

The polypeptide can be purified starting from the host cells' culture medium, according to methods well known to a person skilled in the art such as precipitation with the help of chaotropic agents such as salts, in particular ammonium sulfate, ethanol, acetone or trichloroacetic acid, acid extraction; ion exchange chromatography; phosphocellulose chromatography; hydrophobic interaction chromatography; affinity chromatography; hydroxyapatite chromatography or exclusion chromatographies.

"Culture medium" is understood as the medium in which the polypeptide of the invention is isolated or purified. This medium can be composed of the extracellular medium and/or the cellular lysate. Techniques well known to a person skilled in the art equally permit the latter to give back an active conformation to the polypeptide, if the conformation of said polypeptide was altered during the isolation or the purification.

Antibodies

The present invention also has for its object a process for obtaining an immunospecific antibody.

"Antibody" is understood as the monoclonal, polyclonal, chimeric, simple chain, humanized antibodies as well as the Fab fragments, including Fab or immunoglobulin expression library products.

An immunospecific antibody can be obtained by immunization of an animal with a polypeptide according to the invention.

The invention also relates to an immunospecific antibody for a polypeptide according to the invention, such as defined previously.

A polypeptide according to the invention, one of its fragments, an analog, one of its variants or a cell expressing this polypeptide can also be used to produce immunospecific antibodies.

The term "immunospecific" means that the antibody possesses a better affinity for the polypeptide of the invention than for other polypeptides known in the prior art.

The immunospecific antibodies can be obtained by administration of a polypeptide of the invention, of one of its fragments, of an analog or of an epitopic fragment or of a cell expressing this polynucleotide in a mammal, preferably non human, according to methods well known to a person skilled in the art.

For the preparation of monoclonal antibodies, typical methods for antibody production can be used, starting from cell lines, such as the hybridoma technique (Kohler et al., Nature (1975) 256: 495-497), the trioma technique, the human B cell hybridoma technique (Kozbor et al., Immunology Today (1983) 4: 72) and the EBV hybridoma technique (Cole et al., "The EBV-hybridoma technique and its application to human lung cancer," in Monoclonal Antibodies and Cancer Therapy (Vol. 27, UCLA Symposia on Molecular and Cellular Biology, New Series) (eds. R. A. Reisfeld and S. Sell), pp. 77-96, Alan R. Liss, Inc. N.Y., 1985, pp. 77-96).

The techniques of single chain antibody production such as described, for example, in U.S. Pat. No. 4,946,778 can equally be used.

Transgenic animals such as mice, for example, can equally be used to produce humanized antibodies.

Agents Interacting with the Polypeptide of the Invention

The present invention equally has for its object a method for identifying an agent among one or more compounds to be tested which activates or inhibits the activity of a polypeptide according to the invention, comprising:

a) providing host cells comprising a recombinant vector comprising a polynucleotide according to the invention containing at least one coding SNP;

b) contacting said host cells with said compounds to be tested, c) determining the activating or inhibiting effect upon the activity of said polypeptide whereby said activating or inhibiting agent is identified.

A polypeptide according to the invention can also be employed for a method for screening compounds that interact with it.

These compounds can be activating (agonists) or inhibiting (antagonists) agents of intrinsic activity of a polypeptide according to the invention. These compounds can equally be ligands or substrates of a polypeptide of the invention. See Coligan et al., Current Protocols in Immunology 1 (2), Chapter 5 (1991).

In general, in order to implement such a method, it is first desirable to produce appropriate host cells that express a polypeptide according to the invention. Such cells can be, for example, cells of mammals, yeasts, insects such as *Drosophila* or bacteria such as *E. coli*.

These cells or membrane extracts of these cells are then put in the presence of compounds to be tested.

The binding capacity of the compounds to be tested with the polypeptide of the invention can then be observed, as well as the inhibition or the activation of the functional response.

Step c) of the above method can be implemented by using an agent to be tested that is directly or indirectly labeled. It can also include a competition test, by using a labeled or non-labeled agent and a labeled competitor agent.

It can equally be determined if an agent to be tested generates an activation or inhibition signal on cells expressing the polypeptide of the invention by using detection means appropriately chosen according to the signal to be detected.

Such activating or inhibiting agents can be polynucleotides, and in certain cases oligonucleotides or polypeptides, such as proteins or antibodies, for example.

The present invention also has for its object a method for identifying an agent among one or more compounds to be tested whose activity is potentiated or inhibited by a polypeptide according to the invention, comprising:

a) providing host cells comprising a recombinant vector comprising a polynucleotide according to the invention containing at least one coding SNP;
b) contacting said host cells with said compounds to be tested,
c) determining the potentiating or inhibiting effect upon the activity of said agent whereby said potentiated or inhibited agent is identified.

An agent potentiated or inhibited by the polypeptide of the invention is an agent that responds, respectively, by an activation or an inhibition in the presence of this polypeptide.

The agents, potentiated or inhibited directly or indirectly by the polypeptide of the invention, can consist of polypeptides such as, for example, membranal or nuclear receptors, kinases and more preferably tyrosine kinases, transcription factor or polynucleotides.

Detection of Diseases

The present invention also has for object a method for analyzing the biological characteristics of a polynucleotide according to the invention and/or of a polypeptide according to the invention in a subject, comprising at least one of the following:

a) Determining the presence or the absence of a polynucleotide according to the invention in the genome of a subject;
b) Determining the level of expression of a polynucleotide according to the invention in a subject;
c) Determining the presence or the absence of a polypeptide according to the invention in a subject;
d) Determining the concentration of a polypeptide according to the invention in a subject; and/or
e) Determining the functionality of a polypeptide according to the invention in a subject.

These biological characteristics may be analyzed in a subject or in a sample from a subject.

These biological characteristics may permit to carry out a genetic diagnosis and to determine whether a subject is affected or at risk of being affected or, to the contrary, presents a partial resistance to the development of a disease, an indisposition or a disorder linked to the presence of a polynucleotide according to the invention and/or a polypeptide according to the invention.

These diseases can be disorders and/or human diseases, such as cancers and tumors, infectious diseases, venereal diseases, immunologically related diseases and/or autoimmune diseases and disorders, cardiovascular diseases, metabolic diseases, central nervous system diseases, and disorders connected with chemotherapy treatments.

Said cancers and tumors include carcinomas comprising metastasizing renal carcinomas, melanomas, lymphomas comprising follicular lymphomas and cutaneous T cell lymphoma, leukemias comprising hairy-cell leukemia, chronic lymphocytic leukemia and chronic myeloid leukemia, cancers of the liver, neck, head and kidneys, multiple myelomas, carcinoid tumors and tumors that appear following an immune deficiency comprising Kaposi's sarcoma in the case of AIDS.

Said infectious diseases include viral infections comprising chronic hepatitis B and C and HIV/AIDS, infectious pneumonias, and venereal diseases, such as genital warts.

Said immunologically and auto-immunologically related diseases may include the rejection of tissue or organ grafts, allergies, asthma, psoriasis, rheumatoid arthritis, multiple sclerosis, Crohn's disease and ulcerative colitis.

Said metabolic diseases may include such non-immune associated diseases as obesity.

Said diseases of the central nervous system may include Alzheimer's disease, Parkinson's disease, schizophrenia and depression.

Said diseases and disorders may also include healing of wounds, anemia in dialyzed patient, and osteoporosis.

This method also permits genetic diagnosis of a disease or of a resistance to a disease linked to the presence, in a subject, of the mutant allele encoded by a SNP according to the invention.

Preferably, in step a), the presence or absence of a polynucleotide, containing at least one coding SNP such as previously defined, is going to be detected.

The detection of the polynucleotide may be carried out starting from biological samples from the subject to be studied, such as cells, blood, urine, saliva, or starting from a biopsy or an autopsy of the subject to be studied. The genomic DNA may be used for the detection directly or after a PCR amplification, for example. RNA or cDNA can equally be used in a similar fashion.

It is then possible to compare the nucleotide sequence of a polynucleotide according to the invention with the nucleotide sequence detected in the genome of the subject.

The comparison of the nucleotide sequences can be carried out by sequencing, by DNA hybridization methods, by mobility difference of the DNA fragments on an electrophoresis gel with or without denaturing agents or by melting temperature difference. See Myers et al., Science (1985) 230: 1242. Such modifications in the structure of the nucleotide sequence at a precise point can equally be revealed by nuclease protection tests, such as RNase and the S1 nuclease or also by chemical cleaving agents. See Cotton et al., Proc. Nat. Acad. Sci. USA (1985) 85: 4397-4401. Oligonucleotide probes comprising a polynucleotide fragment of the invention can equally be used to conduct the screening.

Many methods well known to a person skilled in the art can be used to determine the expression of a polynucleotide of the invention and to identify the genetic variability of this polynucleotide (See Chee et al., Science (1996), Vol 274, pp 610-613).

In step b), the level of expression of the polynucleotide may be measured by quantifying the level of RNA encoded by this polynucleotide (and coding for a polypeptide) according to methods well known to a person skilled in the art as, for example, by PCR, RT-PCR, RNase protection, Northern blot, and other hybridization methods.

In step c) and d) the presence or the absence as well as the concentration of a polypeptide according to the invention in a subject or a sample from a subject may be carried out by well known methods such as, for example, by radioimmunoassay, competitive binding tests, Western blot and ELISA tests.

Consecutively to step d), the determined concentration of the polypeptide according to the invention can be compared with the natural wild-type protein concentration usually found in a subject.

A person skilled in the art can identify the threshold above or below which appears the sensitivity or, to the contrary, the resistance to the disease, the indisposition or the disorder evoked above, with the help of prior art publications or by conventional tests or assays, such as those that are previously mentioned.

In step e), the determination of the functionality of a polypeptide according to the invention may be carried out by methods well known to a person skilled in the art as, for example, by in vitro tests such as above mentioned or by an use of host cells expressing said polypeptide.

The present invention also has as an object a diagnostic kit comprising one or more of: an isolated polynucleotide according to the invention; a previously defined recombinant vector; a previously defined host cell; a polypeptide according to the invention; a previously defined antibody.

Therapeutic Compounds and Treatments of Diseases

The present invention also has for its object a therapeutic compound containing, by way of active agent, a polypeptide according to the invention.

The invention also relates to the use of a polypeptide according to the invention, for the manufacture of a therapeutic compound intended for the prevention or the treatment of different human disorders and/or diseases. These diseases can be disorders and/or human diseases, such as cancers and tumors, infectious diseases, venereal diseases, immunologically related diseases and/or autoimmune diseases and disorders, cardiovascular diseases, metabolic diseases, central nervous system diseases, and disorders connected with chemotherapy treatments.

Said cancers and tumors include carcinomas comprising metastasizing renal carcinomas, melanomas, lymphomas comprising follicular lymphomas and cutaneous T cell lymphoma, leukemias comprising hairy-cell leukemia, chronic lymphocytic leukemia and chronic myeloid leukemia, cancers of the liver, neck, head and kidneys, multiple myelomas, carcinoid tumors and tumors that appear following an immune deficiency comprising Kaposi's sarcoma in the case of AIDS.

Said infectious diseases include viral infections comprising chronic hepatitis B and C and HIV/AIDS, infectious pneumonias, and venereal diseases, such as genital warts.

Said immunologically and auto-immunologically related diseases may include the rejection of tissue or organ grafts, allergies, asthma, psoriasis, rheumatoid arthritis, multiple sclerosis, Crohn's disease and ulcerative colitis.

Said metabolic diseases may include such non-immune associated diseases as obesity.

Said diseases of the central nervous system may include Alzheimer's disease, Parkinson's disease, schizophrenia and depression.

Said diseases and disorders may also include healing of wounds, anemia in dialyzed patient, and osteoporosis.

Preferably, a polypeptide according to the invention can also be used for the manufacture of a therapeutic compound intended for the prevention or the treatment of different human disorders and/or diseases, such as certain viral infections such as chronic hepatitis B and C, leukemias such as hairy-cell leukemia and chronic myeloid leukemia, multiple myelomas, follicular lymphomas, carcinoid tumors, malignant melanomas, metastasizing renal carcinomas, Alzheimer's disease, Parkinson's disease, as well as tumors that appear following an immune deficiency, such as Kaposi's sarcoma in the case of AIDS, and genital warts or venereal diseases.

Certain of the compounds permitting to obtain the polypeptide according to the invention as well as the compounds obtained or identified by or from this polypeptide can likewise be used for the therapeutic treatment of the human body, i.e. as a therapeutic compound.

This is why the present invention also has for an object a medicament containing, by way of active agent, a polynucleotide according to the invention containing at least one previously defined coding SNP, a previously defined recombinant vector, a previously defined host cell, and/or a previously defined antibody.

The invention also relates to the use of a polynucleotide according to the invention containing at least one previously defined coding SNP, a previously defined recombinant vector, a previously defined host cell, and/or a previously defined antibody for the manufacture of a medicament intended for the prevention or the treatment of different human disorders and/or diseases. These diseases can be disorders and/or human diseases, such as cancers and tumors, infectious diseases, venereal diseases, immunologically related diseases and/or autoimmune diseases and disorders, cardiovascular diseases, metabolic diseases, central nervous system diseases, and disorders connected with chemotherapy treatments.

Said cancers and tumors include carcinomas comprising metastasizing renal carcinomas, melanomas, lymphomas comprising follicular lymphomas and cutaneous T cell lymphoma, leukemias comprising hairy-cell leukemia, chronic lymphocytic leukemia and chronic myeloid leukemia, cancers of the liver, neck, head and kidneys, multiple myelomas, carcinoid tumors and tumors that appear following an immune deficiency comprising Kaposi's sarcoma in the case of AIDS.

Said infectious diseases include viral infections comprising chronic hepatitis B and C and HIV/AIDS, infectious pneumonias, and venereal diseases, such as genital warts.

Said immunologically and auto-immunologically related diseases may include the rejection of tissue or organ grafts, allergies, asthma, psoriasis, rheumatoid arthritis, multiple sclerosis, Crohn's disease and ulcerative colitis.

Said metabolic diseases may include such non-immune associated diseases as obesity.

Said diseases of the central nervous system may include Alzheimer's disease, Parkinson's disease, schizophrenia and depression.

Said diseases and disorders may also include healing of wounds, anemia in dialyzed patient, and osteoporosis.

Preferably, the invention concerns the use of a polynucleotide according to the invention containing at least one previously defined SNP, a previously defined recombinant vector, a previously defined host cell, and/or a previously defined antibody, for the manufacture of a medicament intended for the prevention or the treatment of different human disorders and/or diseases, such as certain viral infections such as chronic hepatitis B and C, leukemias such as hairy-cell leukemia and chronic myeloid leukemia, multiple myelomas, follicular lymphomas, carcinoid tumors, malignant melanomas, metastasizing renal carcinomas, Alzheimer's disease, Parkinson's disease, as well as tumors that appear following an immune deficiency, such as Kaposi's sarcoma in the case of AIDS, and genital warts or venereal diseases.

The dosage of a polypeptide and of the other compounds of the invention, useful as active agent, depends on the choice of the compound, the therapeutic indication, the mode of administration, the nature of the formulation, the nature of the subject and the judgment of the doctor.

When it is used as active agent, a polypeptide according to the invention is generally administered at doses ranging between 1 and 100 µg/kg of the subject.

The invention also has as an object a pharmaceutical composition that contains, as active agent, at least one above-mentioned compound such as a polypeptide according to the invention, a polynucleotide according to the invention containing at least one previously defined SNP, a previously defined recombinant vector, a previously defined host cell, and/or a previously defined antibody, as well as a pharmaceutically acceptable excipient.

In these pharmaceutical compositions, the active agent is advantageously present at physiologically effective doses.

These pharmaceutical compositions can be, for example, solids or liquids and be present in pharmaceutical forms currently used in human medicine such as, for example, simple or coated tablets, gelcaps, granules, caramels, suppositories and preferably injectable preparations and powders for injectables. These pharmaceutical forms can be prepared according to usual methods.

The active agent(s) can be incorporated into excipients usually employed in pharmaceutical compositions such as talc, Arabic gum, lactose, starch, dextrose, glycerol, ethanol, magnesium stearate, cocoa butter, aqueous or non-aqueous vehicles, fatty substances of animal or vegetable origin, paraffinic derivatives, glycols, various wetting agents, dispersants or emulsifiers, preservatives.

The active agent(s) according to the invention can be employed alone or in combination with other compounds such as therapeutic compounds such as other cytokines such as interleukins or interferons, for example.

The different formulations of the pharmaceutical compositions are adapted according to the mode of administration.

The pharmaceutical compositions can be administered by different routes of administration known to a person skilled in the art.

The present invention also concerns a method for preventing or treating in an individual a disease selected from the group consisting of cancers and tumors, infectious diseases, immunologically and auto-immunologically related diseases, cardiovascular diseases, metabolic diseases, central nervous system diseases, and disorders connected with chemotherapy treatments, comprising administering to said individual a therapeutically effective amount of the previously defined agent, plus a pharmaceutically acceptable excipient.

The invention equally has for an object a diagnostic composition that contains, as active agent, at least one above-mentioned compound such as a polypeptide according to the invention, a polynucleotide according to the invention, a previously defined recombinant vector, a previously defined host cell, and/or a previously defined antibody, as well as a suitable pharmaceutically acceptable excipient.

This diagnostic composition may contain, for example, an appropriate excipient like those generally used in the diagnostic composition such as buffers and preservatives.

The present invention equally has as an object the use:
a) of a therapeutically effective quantity of a polypeptide according to the invention, and/or
b) of a polynucleotide according to the invention, and/or
c) of a host cell from the subject to be treated, previously defined, to prepare a therapeutic compound intended to increase the expression or the activity, in a subject, of a polypeptide according to the invention.

Thus, to treat a subject who needs an increase in the expression or in the activity of a polypeptide of the invention, several methods are possible.

It is possible to administer to the subject a therapeutically effective quantity of a polypeptide of the invention, with a pharmaceutically acceptable excipient.

It is likewise possible to increase the endogenous production of a polypeptide of the invention by administration to the subject of a polynucleotide according to the invention. For example, this polynucleotide can be inserted in a retroviral expression vector. Such a vector can be isolated starting from cells having been infected by a retroviral plasmid vector containing RNA encoding for the polypeptide of the invention, in such a fashion that the transduced cells produce infectious viral particles containing the gene of interest. See Gene Therapy and other Molecular Genetic-based Therapeutic Approaches, Chapter 20, in Human Molecular Genetics, Strachan and Read, BIOS Scientifics Publishers Ltd (1996).

In accordance with the invention, a polynucleotide containing at least one coding SNP such as previously defined will be preferably used.

It is equally possible to administer to the subject host cells belonging to him, these host cells having been preliminarily taken and modified so as to express the polypeptide of the invention, as previously described.

The present invention equally relates to the use:
a) of a therapeutically effective quantity of a previously defined immunospecific antibody, and/or
b) of a polynucleotide permitting inhibition of the expression of a polynucleotide according to the invention, in order to prepare a therapeutic compound intended to reduce the expression or the activity, in a subject, of a polypeptide according to the invention.

Thus, it is possible to administer to the subject a therapeutically effective quantity of an inhibiting agent and/or of an antibody such as previously defined, possibly in combination, with a pharmaceutically acceptable excipient.

It is equally possible to reduce the endogenous production of a polypeptide of the invention by administration to the subject of a complementary polynucleotide according to the invention permitting inhibition of the expression of a polynucleotide of the invention.

Preferably, a complementary polynucleotide containing at least one coding SNP such as previously defined can be used.

The present invention also concerns a method for increasing or decreasing the activity in a subject of the polypeptide according to the invention comprising administering a therapeutically effective quantity of one or more of: an isolated polynucleotide comprising all or part of the nucleotide sequence SEQ ID NO. 1 provided that such nucleotide sequence comprises at least one SNP selected from the group consisting of a559c, g580a, c667t, c682t, t779c, g1033a, c1084a, g1125a, g1135t, g1161a, t1166c, g1181a, a1212g and a1294c, or a nucleotide sequence complementary to said nucleotide sequence; a recombinant vector comprising said polynucleotide; a host cell comprising said recombinant vector, wherein said host cell may be obtained from said subject to be treated; an isolated polypeptide comprising all or part of amino acid sequence SEQ ID NO. 2 and having at least one coding SNP selected from the group consisting of V10A, D95N, L112I, V129L, F139S, R144K and K182Q; an antibody specific for said polypeptide; and a pharmaceutically acceptable excipient.

The present invention concerns also the use of a INFα-7 protein for the preparation of a medicament for the prevention or the treatment of an individual having a disorder or a disease caused by a IFNα-7 variant linked to the presence in the genome of said individual of a nucleotide sequence having at least 95% identity (preferably, 97% identity, more preferably 99% identity and particularly 100% identity) with the nucleotide sequence SEQ ID NO. 1, provided that said nucleotide sequence comprises one of the following SNPs: a559c, g580a, c667t, c682t, t779c, g1033a, c1084a, g1125a, g1135t, g1161a, t1166c, g1181a, a1212g, and a1294c.

Preferably, said medicament is used for the prevention or the treatment of one of the diseases selected from the group consisting of cancers and tumors, infectious diseases, venereal diseases, immunologically related diseases and/or autoimmune diseases and disorders, cardiovascular diseases, metabolic diseases, central nervous system diseases, and disorders connected with chemotherapy treatments.

Said cancers and tumors include carcinomas comprising metastasizing renal carcinomas, melanomas, lymphomas comprising follicular lymphomas and cutaneous T cell lymphoma, leukemias comprising hairy-cell leukemia, chronic lymphocytic leukemia and chronic myeloid leukemia, cancers of the liver, neck, head and kidneys, multiple myelomas, carcinoid tumors and tumors that appear following an immune deficiency comprising Kaposi's sarcoma in the case of AIDS.

Said infectious diseases include viral infections comprising chronic hepatitis B and C and HIV/AIDS, infectious pneumonias, and venereal diseases, such as genital warts.

Said immunologically and auto-immunologically related diseases may include the rejection of tissue or organ grafts, allergies, asthma, psoriasis, rheumatoid arthritis, multiple sclerosis, Crohn's disease and ulcerative colitis.

Said metabolic diseases may include such non-immune associated diseases as obesity.

Said diseases of the central nervous system may include Alzheimer's disease, Parkinson's disease, schizophrenia and depression.

Said diseases and disorders may also include healing of wounds, anemia in dialyzed patient, and osteoporosis.

The present invention concerns also a method for preventing or treating in an individual a disorder or a disease linked to the presence in the genome of said individual of a polynucleotide according to the invention, comprising administering a therapeutically effective amount of one or more of: an isolated polynucleotide comprising all or part of the nucleotide sequence SEQ ID NO. 1 and having at least one SNP selected from the group consisting of a559c, g580a, c667t, c682t, t779c, g1033a, c1084a, g1125a, g1135t, g1161a, t1166c, g1181a, a1212g and a1294c, or a nucleotide sequence complementary to said nucleotide sequence; a recombinant vector comprising said polynucleotide; a host cell comprising said recombinant vector; an isolated polypeptide comprising all or part of amino acid sequence SEQ ID NO. 2 and having at least one coding SNP selected from the group consisting of V10A, D95N, L112I, V129L, F139S, R144K and K182Q; an antibody specific for said polypeptide; and a pharmaceutically acceptable excipient.

Mimetic Compounds of an IFNα-7 Polypeptide Comprising the SNP D95N of the Invention The present invention also concerns a new compound having a biological activity substantially similar to that of the polypeptide of:
  a) amino acid sequence SEQ ID NO. 2, or
  b) amino acid sequence comprising the amino acids included between positions 24 and 189 of the amino acid sequence SEQ ID NO. 2, provided that said amino acid sequences under a) and b) comprise the SNP D95N.

Said biological activity may be evaluated, for example, by measuring signal transduction, dendritic cell maturation, cytokine release by CD4+ or CD8+ T-lymphocytes, cytokine release by monocytes, in vitro or in vivo antiviral activity, anti-tumoral activity in mice previously inoculated with malignant Friend erythroleukemia cells, cellular antiproliferative activity on Daudi Burkitt's cell line, cellular antiproliferative activity on TF-1 cell line, as described in the experimental section.

As mentioned in the experimental section, the D95N mutated IFNα-7 shows:
  a weak capacity to stimulate dendritic cell maturation
  a high capacity to stimulate cytokine release (IFN gamma and IL-10) by CD4+ T-lymphocytes and CD8+ T-lymphocytes preactivated by SEB antigen
  a capacity to stimulate cytokine (IL-10, IL-12, and TNF-α) release by monocytes
  a weak antiproliferative activity on TF-1 cells
  an antiviral activity in vitro in cell culture infected with VSV
  a high antiviral activity in vivo in mice infected with EMCV
  an anti-tumoral activity in FLC-inoculated mice Also as mentioned in the experimental section, in comparison to wild-type IFNα-2, the D95N mutated IFNα-7 protein possesses:
  a similar capacity to activate signal transduction
  a lower capacity to stimulate dendritic cell maturation
  a higher capacity to stimulate IFN gamma release by CD4+ T-lymphocytes and CD8+ T-lymphocytes preactivated by SEB antigen
  a higher capacity to stimulate IL-10 and TNF-α release by monocytes
  a similar antiproliferative activity on TF-1 cells
  a lower antiviral activity in vitro in cell culture infected with VSV
  a higher antiviral activity in vivo in mice infected with EMCV
  a slightly lower anti-tumoral activity in FLC-inoculated mice Also as mentioned in the experimental section, in comparison to wild-type IFNα-7, the D95N mutated INFα-7 protein possesses:
  a similar capacity to activate signal transduction
  a slightly higher capacity to inhibit Daudi cell proliferation.

A new compound of the invention, such as previously defined, may possess a biological activity substantially similar to that of the D95N mutated IFNα-7.

Said compound may also have a biological activity, such as IFN-gamma release by T-lymphocytes, IL-10 and TNF-α release by monocytes, in vivo antiviral activity in mice infected with EMCV, and/or an anti-tumoral activity in FLC-inoculated mice, which is even higher than that of the D95N mutated INFα-7.

Said compound may also have a biological activity, such as dendritic cell maturation, which is even lower than that of the D95N mutated INFα-7.

Said compound may be a biochemical compound, such as a polypeptide or a peptide for example, or an organic chemical compound, such as a synthetic peptide-mimetic for example.

The present invention also concerns the use of a polypeptide of the invention containing the D95N SNP, for the identification of a compound such as defined above.

The present invention also concerns a method for the identification of a compound of the invention, comprising the following steps:

a) Determining the biological activity of the compound to be tested, such as signal transduction, dendritic cell maturation, cytokine release by CD4+ or CD8+ T-lymphocytes, cytokine release by monocytes, in vitro or in vivo antiviral activity, anti-tumoral activity in mice previously inoculated with malignant Friend erythroleukemia cells, cellular antiproliferative activity on Daudi Burkitt's cell line, cellular antiproliferative activity on TF-1 cell line, for example;

b) Comparing:
  i) the activity determined in step a) of the compound to be tested, with
  ii) the activity of the polypeptide of amino acid sequence SEQ ID NO. 2, or of amino acid sequence comprising the amino acids included between positions 24 and 189 of the amino acid sequence SEQ ID NO. 2; provided that said amino acid sequences comprise the D95N SNP; and c) Determining on the basis of the comparison carried out in step b) whether the compound to be tested has a substantially similar, or lower or higher, activity compared to that of the polypeptide of amino acid sequence SEQ ID NO. 2, or of amino acid sequence comprising the amino acids included between positions 24 and 189 of the amino acid sequence SEQ ID NO. 2; provided that said amino acid sequences comprise the D95N SNP.

Preferably, the compound to be tested may be previously identified from synthetic peptide combinatorial libraries, high-throughput screening, or designed by computer-aided drug design so as to have the same three-dimensional structure as that of the polypeptide of amino acid sequence SEQ ID NO. 2, or of amino acid sequence comprising the amino acids included between positions 24 and 189 of the amino acid sequence SEQ ID NO. 2; provided that said amino acid sequences comprise the D95N SNP.

The methods to identify and design compounds are well known by a person skilled in the art.

Publications referring to these methods may be, for example:

Silverman R. B. (1992). "Organic Chemistry of Drug Design and Drug Action". Academic Press, 1st edition (Jan. 15, 1992).

Anderson S and Chiplin J. (2002). "Structural genomics; shaping the future of drug design" Drug Discov. Today. 7(2): 105-107.

Selick H E, Beresford A P, Tarbit M H. (2002). "The emerging importance of predictive ADME simulation in drug discovery". Drug Discov. Today. 7(2):109-116.

Burbidge R, Trotter M, Buxton B, Holden S. (2001). "Drug design by machine learning: support vector machines for pharmaceutical data analysis". Comput. Chem. 26(1): 5-14.

Kauvar L. M. (1996). "Peptide mimetic drugs: a comment on progress and prospects" 14(6): 709.

The compounds of the invention may be used for the preparation of a medicament intended for the prevention or the treatment of one of the diseases selected from the group consisting of cancers and tumors, infectious diseases, venereal diseases, immunologically related diseases and/or autoimmune diseases and disorders, cardiovascular diseases, metabolic diseases, central nervous system diseases, and disorders connected with chemotherapy treatments.

Said cancers and tumors include carcinomas comprising metastasizing renal carcinomas, melanomas, lymphomas comprising follicular lymphomas and cutaneous T cell lymphoma, leukemias comprising hairy-cell leukemia, chronic lymphocytic leukemia and chronic myeloid leukemia, cancers of the liver, neck, head and kidneys, multiple myelomas, carcinoid tumors and tumors that appear following an immune deficiency comprising Kaposi's sarcoma in the case of AIDS.

Said infectious diseases include viral infections comprising chronic hepatitis B and C and HIV/AIDS, infectious pneumonias, and venereal diseases, such as genital warts.

Said immunologically and auto-immunologically related diseases may include the rejection of tissue or organ grafts, allergies, asthma, psoriasis, rheumatoid arthritis, multiple sclerosis, Crohn's disease and ulcerative colitis.

Said metabolic diseases may include such non-immune associated diseases as obesity.

Said diseases of the central nervous system may include Alzheimer's disease, Parkinson's disease, schizophrenia and depression.

Said diseases and disorders may also include healing of wounds, anemia in dialyzed patient, and osteoporosis.

Preferably, the compounds of the invention may be used for the preparation of a medicament intended for the prevention or the treatment of one of the diseases selected from the group consisting of certain viral infections such as chronic hepatitis B and C, leukemias such as hairy-cell leukemia and chronic myeloid leukemia, multiple myelomas, follicular lymphomas, carcinoid tumors, malignant melanomas, metastasizing renal carcinomas, Alzheimer's disease, Parkinson's disease, as well as tumors that appear following an immune deficiency, such as Kaposi's sarcoma in the case of AIDS, and genital warts or venereal diseases.

Experimental Section

EXAMPLE 1

Modeling of a Protein Encoded by a Polynucleotide of Nucleotide Sequence Containing SNP g1033a, t1166c, g1181a, or a1294c, and of the Protein Encoded by the Nucleotide Sequence of the Wild-Type Reference Gene In a first step the three-dimensional structure of IFNα-7 was constructed starting from that of IFNα-2 whose structure is available in the PDB database (code 1ITF) and by using the software Modeler (MSI, San Diego, Calif.).

The mature polypeptide fragment was then modified in such a fashion as to reproduce the mutation D72N, F116S, R121K, or K159Q.

A thousand molecular minimization steps were conducted on this mutated fragment by using the programs AMBER and DISCOVER (MSI: Molecular Simulations Inc.).

Two molecular dynamic calculation runs were then carried out with the same program and the same force fields.

In each case, 50,000 steps were calculated at 300° K, terminated by 300 equilibration steps.

The results of these modelings are visualized on FIGS. 1, 2, 3 and 4.

EXAMPLE 2

Genotyping of the SNPs t779c, g1033a, c1084a, g1135t, t1166c, g1181a or a1294c in a Population of Individuals The genotyping of SNPs is based on the principle of the minisequencing wherein the product is detected by a reading of polarized fluorescence. The technique consists of a fluorescent minisequencing (FP-TDI Technology or Fluorescence Polarization Template-direct Dye-terminator Incorporation).

The minisequencing is performed on a product amplified by PCR from genomic DNA of each individual of the population. This PCR product is chosen in such a manner that it covers the genic region containing the SNP to be genotyped. After elimination of the PCR primers that have not been used and the dNTPs that have not been incorporated, the minisequencing is carried out.

The minisequencing consists of lengthening an oligonucleotide primer, placed just upstream of the site of the SNP, by using a polymerase enzyme and fluorolabeled dideoxynucleotides. The product resulting from this lengthening process is directly analyzed by a reading of polarized fluorescence.

All these steps, as well as the reading, are carried out in the same PCR plate.

Thus, the genotyping requires 5 steps:
1) Amplification by PCR
2) Purification of the PCR product by enzymatic digestion
3) Elongation of the oligonucleotide primer
4) Reading
5) Interpretation of the reading The genotyping steps 1 and 2 are carried out in the same conditions for each of the SNPs t779c, g1033a, c1084a, g1135t, t1166c, g1181a and a1294c. The steps 3, 4 and 5 are specific to each one of these polymorphisms.

1) The PCR amplification of the nucleotide sequence of the IFNα-7 gene is carried out starting from genomic DNA coming from 268 individuals of ethnically diverse origins.

These genomic DNAs were provided by the Coriell Institute in the United States.

The 268 individuals are distributed as follows:

TABLE 1

| Phylogenic Population | Specific Ethnic Population | Total | % |
|---|---|---|---|
| African American | African American | 50 | 100.0 |
|  | Subtotal | 50 | 18.7 |
| Amerind | South American Andes | 10 | 66.7 |
|  | South West American Indians | 5 | 33.3 |
|  | Subtotal | 15 | 5.6 |
| Caribbean | Caribbean | 10 | 100.0 |
|  | Subtotal | 10 | 3.7 |
| European Caucasoid | North American Caucasian | 79 | 79.8 |
|  | Iberian | 10 | 10.1 |
|  | Italian | 10 | 10.1 |
|  | Subtotal | 99 | 36.9 |
| Mexican | Mexican | 10 | 100.0 |
|  | Subtotal | 10 | 3.7 |
| Northeast Asian | Chinese | 10 | 50.0 |
|  | Japanese | 10 | 50.0 |
|  | Subtotal | 20 | 7.5 |
| Non-European Caucasoid | Greek | 8 | 21.6 |
|  | Indo-Pakistani | 9 | 24.3 |
|  | Middle-Eastern | 20 | 54.1 |
|  | Subtotal | 37 | 13.8 |

TABLE 1-continued

| Phylogenic Population | Specific Ethnic Population | Total | % |
|---|---|---|---|
| Southeast Asian | Pacific Islander | 7 | 41.2 |
|  | South Asian | 10 | 58.8 |
|  | Subtotal | 17 | 6.3 |
| South American | South American | 10 | 100.0 |
|  | Subtotal | 10 | 3.7 |
|  | Total | 268 | 100 |

The genomic DNA coming from each one of these individuals constitutes a sample.

For all the SNPs, the PCR amplification is carried out starting from the following primers:

```
SEQ ID NO. 3:   Sense       TACCCACCTCAGGTAGCC
                primer:

SEQ ID NO. 4:   Antisense   CATGAAAGTGTGAGATGATGC
                primer:
```

These nucleotide sequences permit amplification of a fragment having a length of 669 nucleotides, from nucleotide 711 to nucleotide 1379 in the nucleotide sequence SEQ ID NO. 1.

For each SNP, the PCR product will serve as a template for the minisequencing

The total reaction volume of the PCR reaction is 5 µl per sample.

This reaction volume is composed of the reagents indicated in the following table:

TABLE 2

| Supplier | Reference | Reactant | Initial Conc. | Vol. per tube (µl) | Final Conc. |
|---|---|---|---|---|---|
| Life Technology | Delivered with Taq | Buffer (X) | 10 | 0.5 | 1 |
| Life Technology | Delivered with Taq | MgSO$_4$ (mM) | 50 | 0.2 | 2 |
| AP Biotech | 27-2035-03 | dNTPs (mM) | 10 | 0.1 | 0.2 |
|  | On request | Sense Primer (µM) | 10 | 0.1 | 0.2 |
|  | On request | Antisense Primer (µM) | 10 | 0.1 | 0.2 |
| Life Technology | 11304-029 | Taq platinum | 5 U/µl | 0.02 | 0.1 U/reaction |
|  |  | H$_2$O | Qsp 5 µl | 1.98 |  |
|  |  | DNA (sample) | 2.5 ng/µl | 2 | 5 ng/reaction |
|  |  | Total volume |  | 5 µl |  |

These reagents are distributed in a black PCR plate having 384 wells provided by ABGene (ref: TF-0384-k). The plate is sealed, centrifuged, then placed in a thermocycler for 384-well plates (Tetrad of MJ Research) and undergoes the following incubation: PCR Cycles: 1 min at 94° C., followed by 36 cycles composed of 3 steps (15 sec. at 94° C., 30 sec. at 56° C., 1 min at 68° C.).

2) The PCR amplified product is then purified using two enzymes: Shrimp Alkaline Phosphatase (SAP) and exonuclease I (Exo I). The first of these enzymes permits the dephosphorylation of the dNTPs which have not been incorporated during the PCR amplification, whereas the second eliminates the single stranded DNA residues, in particular the primers which have not been used during the PCR.

This digestion is done by addition, in each well of the PCR plate, of a reaction mixture of 5 µl per sample. This reaction mixture is composed of the following reagents:

TABLE 3

| Supplier | Reference | Reactant | Initial Conc. | Vol. per tube (µl) | Final conc. |
|---|---|---|---|---|---|
| AP Biotech | E70092X | SAP | 1 U/µl | 0.5 | 0.5/reaction |
| AP Biotech | 070073Z | Exo I | 10 U/µl | 0.1 | 1/reaction |
| AP Biotech | Supplied with SAP | Buffer SAP (X) | 10 | 0.5 | 1 |
| | | H₂O | Qsp 5 µl | 3.9 | |
| | | PCR product | | 5 µl | |
| | | Total vol. | | 10 µl | |

Once filled, the plate is sealed, centrifuged, then placed in a thermocycler for 384 well plates (Tetrad of MJ Research) and undergoes the following incubation: Digestion SAP-EXO: 45 min at 37° C., 15 min at 80° C.

The elongation or minisequencing step is then carried out on the product of PCR digested by addition of a reaction mixture of 5 µl per prepared sample.

The minisequencing 3) and the reading steps 4) and interpretation of reading 5) are specific to each of the SNPs t779c, g1033a, c1084a, g1135t, t1166c, g1181a and a1294c.

All these steps are described hereinafter precising the specific conditions used for each one of these polymorphisms.

3) Minisequencing

The sequences of the minisequencing primers necessary for the genotyping were determined in a way to correspond to the sequence of the nucleotides located upstream of the site of a SNP according to the invention. The PCR product that contains the SNP being a double stranded DNA product, the genotyping can therefore be done either on the sense strand or on the antisense strand. The selected primers are manufactured by Life Technologies Inc.

The following table indicates, for each SNP, the sequence of the minisequencing primers that have been tested and the optimal condition retained for the genotyping:

TABLE 4

| SNP | Primers tested | Optimal condition retained for the genotyping |
|---|---|---|
| t779c | SEQ ID NO. 5: sense primer: gtccttttctttactgatgg SEQ ID NO. 6: antisense primer: tgtagctgagtaccagcacg | sense primer + ddCTP-R110 + ddTTP-Tamra |
| g1033a | SEQ ID NO. 7: Sense primer: tcaatctcttcagcacagag SEQ ID NO. 8: Antisense primer: ttcccaagcagcagatgagt | antisense primer + ddCTP-R110 + ddTTP-Tamra |
| c1084a | SEQ ID NO. 9: sense primer: tagaaaattttccactgaa SEQ ID NO. 10: antisense primer: gtcattcagttgctggtaaa | antisense primer + ddTTP-R110 + ddGTP-Tamra |
| g1135t | SEQ ID NO. 11: sense primer: gtgtgatacaggaggttggg SEQ ID NO. 12: antisense primer: catcagggagtctcttcca | antisense primer + ddATP-R110 + ddCTP-Tamra |
| t1166c | SEQ ID NO. 13: Sense primer: tcccctgatgaatgaggact SEQ ID NO. 14: | antisense primer + dGTP-R110 + ddATP-Tamra |
| g1181a | Antisense primer: atttcctcacagccaggatg SEQ ID NO. 15: Sense primer: ggacttcatcctggctgtga SEQ ID NO. 16: Antisense primer: tgattctttggaagtatttc | sense primer + ddATP-R110 + ddGTP-Tamra |
| a1294c | SEQ ID NO. 17: Sense primer: tctcttttcaacaaacttg SEQ ID NO. 18: Antisense primer: cttcctccttaatccttttt | sense primer + ddCTP-R110 + ddATP-Tamra |

The minisequencing of the SNPs was first validated over 16 samples, then genotyped over the set of the population of individuals composed of 268 individuals and 10 controls.

The elongation or minisequencing step is then carried out as indicated in the following table:

TABLE 5

| Supplier | Reference | Reactant | Initial conc. | Vol. per tube (µl) | Final conc. |
|---|---|---|---|---|---|
| Own preparation | | Elongation Buffer[1] (X) | 5 | 1 | 1 |
| Life Technologies | On request | Miniseq Primer (µM) A or B | 10 | 0.5 | 1 |
| AP Biotech | 27-2051 (61,71,81)-01 | ddNTPs[2] (µM) 2 are non labeled | 2.5 of each | 0.25 | 0.125 of each |
| NEN | Nel 472/5 and Nel 492/5 | ddNTPs[2] (µM) 2 are labeled with Tamra and R110 | 2.5 of each | 0.25 | 0.125 of each |
| AP Biotech | E79000Z | Thermo-sequenase | 3.2 U/µl | 0.125 | 0.4 U/reaction |
| | | H₂O digested PCR product | Qsp 5 µl | 3.125 10 | |
| | | Total volume | | 15 | |

[1]The 5X elongation buffer is composed of 250 mM Tris-HCl pH 9, 250 mM KCl, 25 mM NaCl, 10 mM MgCl₂ and 40% glycerol.
[2]For the ddNTPs, a mixture of the 4 bases is carried out according to the polymorphism studied. Only the 2 bases of interest (wild-type nucleotide/ mutated nucleotide) composing the functional SNP are labeled, either in Tamra, or in R110. For example, for SNP g1033a, the mixture of ddNTPs is composed of: 2.5 µM of ddATP non labeled, 2.5 µM of ddGTP non-labeled, 2.5 µM of ddTTP (1.875 µM of ddTTP non labeled and 0.625 µM of ddTTP Tamra labeled), 2.5 µM of ddCTP (1.875 µM of ddCTP non labeled and 0.625 µM of ddCTP R110 labeled).

Once filled, the plate is sealed, centrifuged, then placed in a thermocycler for 384-well plates (Tetrad of MJ Research) and undergoes the following incubation: Elongation cycles: 1 min. at 93° C., followed by 35 cycles composed of 2 steps (10 sec. at 93° C., 30 sec. at 55° C.).

After the last step in the thermocycler, the plate is directly placed on a polarized fluorescence reader of type Analyst® HT of LJL Biosystems Inc. The plate is read //using Criterion Host® software by using two methods. The first permits reading the Tamra labeled base by using emission and excitation filters specific for this fluorophore (excitation 550-10 nm, emission 580-10 nm) and the second permits reading the R110 labeled base by the excitation and emission filters specific for this fluorophore (excitation 490-10 nm, emission 520-10 nm). In the two cases, a dichroic double mirror (R 110/Tamra) is used and the other reading parameters are:

Z-height: 1.5 mm
Attenuator: out
Integration time: 100,000 μsec.
Raw data units: counts/sec
Switch polarization: by well
Plate settling time: 0 msec
PMT setup: Smart Read (+), sensitivity 2
Dynamic polarizer: emission
Static polarizer: S A file result is thus obtained containing the calculated values of MP (milliPolarization) for the Tamra filter and that for the R110 filter. These mP values are calculated starting from intensity values obtained on the parallel plane (//) and on the perpendicular plane (⊥) according to the following formula:

$$MP = 1000(// - g\perp)/(// + g\perp).$$

In this calculation, the value ⊥ is weighted by a factor g. It is a machine parameter that must be determined experimentally beforehand.

4) and 5) Interpretation of the reading and determination of the genotypes.

The mP values are reported on a graph using Microsoft Inc. Excel software, and/or Allele Caller® software developed by LJL Biosystems Inc.

On the abscissa is indicated the mP value of the Tamra labeled base, on the ordinate is indicated the mP value of the R110 labeled base. A strong mP value indicates that the base labeled with this fluorophore is incorporated and, conversely, a weak mP value reveals the absence of incorporation of this base.

Up to three homogenous groups of nucleotide sequences having different genotypes may be obtained.

The use of the Allele Caller® software permits, once the identification of the different groups is carried out, to directly extract the genotype defined for each individual in table form.

It is necessary to specify that for SNP g1033a, for example, the allele c read in antisense corresponds to the allele g read in sense, and is related to the presence of an aspartic acid (D) at position 95 of the immature INFα-7 protein sequence and therefore that the allele t read in antisense corresponds to the allele a read in sense corresponding to an asparagine (N) for this position in the sequence of the corresponding protein.

Results of the Minisequencing for the SNPs t779c, g1033a, c1084a, g1135t, t1166c, g1181a and a1294c After the completion of the genotyping process, the determination of the genotypes of the individuals of the population of individuals for the SNPs studied here was carried out using the graphs described above.

For SNP t779c, the genotype is in theory either homozygote TT, or heterozygote TC, or homozygote CC in the tested individuals. In reality, and as shown below, the homozygote genotype CC is not detected in the population of individuals.

For SNP g1033a, the genotype is in theory either homozygote GG, or heterozygote GA, or homozygote AA in the tested individuals. In reality, and as shown below, the homozygote genotype AA is not detected in the population of individuals.

For SNP g1135t, the genotype is in theory either homozygote GG, or heterozygote GT, or homozygote TT in the tested individuals. In reality, and as shown below, the homozygote genotype TT is not detected in the population of individuals.

For SNP c1084a, the genotype is in theory either homozygote CC, or heterozygote CA, or homozygote AA in the tested individuals. In reality, and as shown below, the homozygote genotype AA is not detected in the population of individuals.

For SNP t1166c, the genotype is in theory either homozygote TT, or heterozygote TC, or homozygote CC in the tested individuals. In reality, and as shown below, the homozygote genotype CC is not detected in the population of individuals.

For SNP g1181a, the genotype is in theory either homozygote GG, or heterozygote GA, or homozygote AA in the tested individuals. In reality, and as shown below, the homozygote genotype AA is not detected in the population of individuals.

For SNP a1294c, the genotype is in theory either homozygote AA, or heterozygote AC, or homozygote CC in the tested individuals. In reality, and as shown below, the homozygote genotype CC is not detected in the population of individuals.

The results of the distribution of the determined genotypes in the population of individuals and the calculation of the different allelic frequencies for the 7 studied SNPs are presented in the following tables:

TABLE 6

| Phylogenic Population | Total | f | (95% CI) | TT | % | TC | % | CC | % | Total |
|---|---|---|---|---|---|---|---|---|---|---|
| | | | | t779c (V10A) | | | | | | |
| African American | 50 | | | 50 | 100 | | | | | 50 |
| Amerind | 15 | | | 15 | 100 | | | | | 15 |
| Caribbean | 10 | | | 10 | 100 | | | | | 10 |
| European Caucasoid | 99 | | | 97 | 100 | | | | | 97 |
| Mexican | 10 | | | 9 | 100 | | | | | 9 |
| Non-European Caucasoid | 37 | 2.7 | (0, 6.4) | 35 | 94.6 | 2 | 5.41 | | | 37 |
| Northeast Asian | 20 | | | 20 | 100 | | | | | 20 |
| South American | 10 | | | 10 | 100 | | | | | 10 |
| Southeast Asian | 17 | | | 16 | 100 | | | | | 16 |
| Total | 268 | 0.4 | (0, 0.9) | 262 | 99.2 | 2 | 0.76 | | | 264 |

TABLE 7

| Phylogenic Population | Total | f | (95% CI) | g1033a (D95N) | | | | | | Total |
|---|---|---|---|---|---|---|---|---|---|---|
| | | | | GG | % | GA | % | AA | % | |
| African American | 50 | 4.1 | (0.2, 8.0) | 45 | 91.8 | 4 | 8.16 | | | 49 |
| Amerind | 15 | | | 15 | 100 | | | | | 15 |
| Caribbean | 10 | | | 10 | 100 | | | | | 10 |
| European Caucasoid | 99 | | | 98 | 100 | | | | | 98 |
| Mexican | 10 | | | 10 | 100 | | | | | 10 |
| Non-European Caucasoid | 37 | | | 37 | 100 | | | | | 37 |
| Northeast Asian | 20 | | | 20 | 100 | | | | | 20 |
| South American | 10 | | | 10 | 100 | | | | | 10 |
| Southeast Asian | 17 | | | 16 | 100 | | | | | 16 |
| Total | 268 | 0.8 | (0, 1.5) | 261 | 98.5 | 4 | 1.51 | | | 265 |

TABLE 8

| Phylogenic Population | Total | f | (95% CI) | c1084a (L112I) | | | | | | Total |
|---|---|---|---|---|---|---|---|---|---|---|
| | | | | CC | % | CA | % | AA | % | |
| African American | 50 | 2.1 | (0, 5.0) | 45 | 95.7 | 2 | 4.26 | | | 47 |
| Amerind | 15 | | | 15 | 100 | | | | | 15 |
| Caribbean | 10 | | | 10 | 100 | | | | | 10 |
| European Caucasoid | 99 | | | 92 | 100 | | | | | 92 |
| Mexican | 10 | | | 6 | 100 | | | | | 6 |
| Non-European Caucasoid | 37 | | | 37 | 100 | | | | | 37 |
| Northeast Asian | 20 | | | 20 | 100 | | | | | 20 |
| South American | 10 | | | 10 | 100 | | | | | 10 |
| Southeast Asian | 17 | | | 17 | 100 | | | | | 17 |
| Total | 268 | 0.4 | (0, 0.9) | 252 | 99.2 | 2 | 0.79 | | | 254 |

TABLE 9

| Phylogenic Population | Total | f | (95% CI) | g1135t (V129L) | | | | | | Total |
|---|---|---|---|---|---|---|---|---|---|---|
| | | | | GG | % | GT | % | TT | % | |
| African American | 50 | 2.0 | (0, 4.8) | 47 | 95.9 | 2 | 4.1 | | | 47 |
| Amerind | 15 | | | 15 | 100 | | | | | 15 |
| Caribbean | 10 | 10.0 | (0, 23.1) | 8 | 80.0 | 2 | 20.0 | | | 10 |
| European Caucasoid | 99 | | | 98 | 100 | | | | | 98 |
| Mexican | 10 | 5.6 | (0, 16.1) | 8 | 88.9 | 1 | 11.1 | | | 9 |
| Non-European Caucasoid | 37 | | | 37 | 100 | | | | | 37 |
| Northeast Asian | 20 | | | 20 | 100 | | | | | 20 |
| South American | 10 | | | 10 | 100 | | | | | 10 |
| Southeast Asian | 17 | | | 17 | 100 | | | | | 17 |
| Total | 268 | 0.9 | (0.1, 1.8) | 260 | 98.1 | 5 | 1.9 | | | 263 |

TABLE 10

| Phylogenic Population | Total | f | (95% CI) | t1166c (F139S) | | | | | | Total |
|---|---|---|---|---|---|---|---|---|---|---|
| | | | | TT | % | TC | % | CC | % | |
| African American | 50 | | | 45 | 100 | | | | | 45 |
| Amerind | 15 | | | 15 | 100 | | | | | 15 |
| Caribbean | 10 | 5 | (0, 14.6) | 9 | 90.0 | 1 | 10.0 | | | 10 |
| European Caucasoid | 99 | 1.5 | (0, 3.2) | 96 | 97.0 | 3 | 3.0 | | | 99 |
| Mexican | 10 | | | 9 | 100 | | | | | 9 |
| Non-European Caucasoid | 37 | | | 37 | 100 | | | | | 37 |
| Northeast Asian | 20 | | | 20 | 100 | | | | | 20 |
| South American | 10 | | | 10 | 100 | | | | | 10 |
| Southeast Asian | 17 | 2.9 | (0, 8.6) | 16 | 94.1 | 1 | 5.9 | | | 17 |
| Total | 268 | 1 | (0.1, 1.8) | 257 | 98.1 | 5 | 1.9 | | | 262 |

TABLE 11

| Phylogenic Population | Total | f | (95% CI) | GG | % | GA | % | AA | % | Total |
|---|---|---|---|---|---|---|---|---|---|---|
| | | | | g1181a (R144K) | | | | | | |
| African American | 50 | | | 50 | 100 | | | | | 50 |
| Amerind | 15 | | | 15 | 100 | | | | | 15 |
| Caribbean | 10 | | | 10 | 100 | | | | | 10 |
| European Caucasoid | 99 | | | 99 | 100 | | | | | 99 |
| Mexican | 10 | | | 10 | 100 | | | | | 10 |
| Non-European Caucasoid | 37 | | | 37 | 100 | | | | | 37 |
| Northeast Asian | 20 | | | 20 | 100 | | | | | 20 |
| South American | 10 | | | 10 | 100 | | | | | 10 |
| Southeast Asian | 17 | 2.9 | (0, 8.6) | 16 | 94.1 | 1 | 5.9 | | | 17 |
| Total | 268 | 0.2 | (0, 0.6) | 267 | 99.6 | 1 | 0.4 | | | 268 |

TABLE 12

| Phylogenic Population | Total | f | (95% CI) | AA | % | AC | % | CC | % | Total |
|---|---|---|---|---|---|---|---|---|---|---|
| | | | | a1294c (K182Q) | | | | | | |
| African American | 50 | 2.0 | (0, 4.7) | 48 | 96.0 | 2 | 4.0 | | | 50 |
| Amerind | 15 | | | 15 | 100 | | | | | 15 |
| Caribbean | 10 | | | 10 | 100 | | | | | 10 |
| European Caucasoid | 99 | | | 99 | 100 | | | | | 99 |
| Mexican | 10 | | | 7 | 100 | | | | | 7 |
| Non-European Caucasoid | 37 | | | 37 | 100 | | | | | 37 |
| Northeast Asian | 20 | | | 20 | 100 | | | | | 20 |
| South American | 10 | | | 10 | 100 | | | | | 10 |
| Southeast Asian | 17 | | | 17 | 94.1 | | | | | 17 |
| Total | 268 | 0.4 | (0, 0.9) | 265 | 99.3 | 2 | 0.7 | | | 265 |

In the above tables,

N represents the number of individuals,

% represents the percentage of individuals in the specific sub-population, the allelic frequency represents the percentage of the mutated allele in the specific sub-population, 95% IC represents the minimal and maximal interval of confidence at 95%.

By examining these results by phylogenic population, and by SNP, it is observed that:

for SNP t779c, the 2 heterozygote individuals TC come from the sub-population non-European Caucasoid.

for SNP g1033a, the 4 heterozygote individuals GA come from the sub-population African American.

for SNP c1084a, the 2 heterozygote individuals CA come from the sub-population African American.

for SNP g1135t, the 5 heterozygote individuals GT come from the sub-populations African American, Caribbean, and Mexican.

for SNP t1166c, the 5 heterozygote individuals TC come from the sub-populations Caribbean, European Caucasoid, and Southeast Asian.

for SNP g1181a, the unique heterozygote individual GA comes from the sub-population Southeast Asian.

for SNP a1294c, the 2 heterozygote individuals AC come from the sub-population African American.

EXAMPLE 3

Expression of Natural Wild-type IFNα-7 and Mutated IFNα-7 Proteins in Yeast a) Cloning of the Natural Wild-Type IFNα-7 and Mutated IFNα-7 in the Eukaryote Expression Vector pPicZα-topo The nucleotide sequences coding for the mature part of the natural wild-type IFNα-7, D72N mutated INFα-7, V106L mutated IFNα-7, or K159Q mutated IFNα-7 are amplified by PCR using as template genomic DNA from an individual who is heterozygote for one of said SNPs.

The PCR primers permitting such an amplification are:

SEQ ID NO. 19: Sense primer: TGTGATCTGCCTCAGACCCAC

SEQ ID NO. 20: Antisense primer: TCAATCCTTCCTCCTTAATCCTTTTT

The PCR products are inserted in the eukaryote expression vector pPicZα-TOPO under the control of the hybrid promoter AOX1 inducible by methanol (TOPO™-cloning; Invitrogen Corp.).

This vector permits the heterologous expression of eukaryote proteins in the yeast *Pichia pastoris*.

After checking of the nucleotide sequence of the region of the vector coding for the recombinant proteins, the vector is linearized by the Pme1 restriction enzyme, and the *P. pastoris* yeast strain (Invitrogen) is transformed with these recombinant expression vectors.

b) Heterologous Expression in *P. pastoris* and Purification of the Natural Wild-Type IFNα-7 and Mutated IFNα-7 Proteins Two saturated pre-cultures of 50 mL of BMGY medium (2% Peptone, 1% yeast extract, 1.34% YNB, 1% Glycerol, 100 mM potassium phosphate, 0.4 mg/Liter biotin pH 6.0) containing a clone coding for natural wild-type IFNα-7, or that coding for D72N mutated IFNα-7, V106L mutated IFNα-7, or K159Q mutated IFNα-7, were carried out for 24-48 hours at 30° C. at an agitation of 200 rotations per minute (rpm).

When the culture reaches a saturating cellular density (corresponding to an optical density of 12 measured at a wavelength of 600 nm), it is used to inoculate, at 5 OD/mL, 250 mL of BMMY medium (2% Peptone, 1% yeast extract, 1.34% YNB, 0.5% Methanol, 100 mM potassium phosphate, 0.4 mg/Liter biotin pH 6.0).

The expression of the protein is then induced by methanol at a final concentration of 1%, for 24 hours at 30° C., with an agitation of the culture flask at 180 rpm.

Due to the presence of the signal peptide sequence of the "alpha factor", upstream of the coding sequence, the proteins are secreted by the yeasts in the culture medium. The alpha factor is naturally cleaved during the processing.

The suspension is centrifuged and the protein is purified by HPLC starting from the obtained supernatant.

In a pre-started step, an ultrafiltration (Labscale, cut-off 5000Da, Millipore) followed by a dialysis permits a ten times concentration of the yeast supernatant in a buffer of 50 mM Tris-Cl pH 9.0, 25 mM NaCl.

The first chromatographic step permits protein recovery by affinity on a blue sepharose column (Amersham Pharmacia). The presence of the protein in the collected fractions is verified, on the one hand by electrophoresis of SDS PAGE type and on the other hand by immuno-detection by a specific antibody directed against the IFNα-7 protein. At this step, the purity of the protein of interest is higher than 75%.

In a second purification step, a gel filtration permits buffer exchange of the collected fractions corresponding to IFNα-7 proteins against 50 mM Tris pH 9.0, 25 mM NaCl.

The last step of the purification consists of a separation of the proteins on an ion exchange chromatography column. The fractions containing the recombinant protein are injected on an anion exchange column (ResourceQ 6.0 mL, Pharmacia) equilibrated beforehand in Tris 50 mM pH 9, NaCl 25 mM buffer. The elution of the proteins is carried out by the migration of a gradient between 0.025 and 1 M NaCl in the Tris 50 mM pH 9 buffer. Alternatively, the purification may be performed using blue cibacron.

The purity of the protein of interest is estimated on SDS/PAGE gel and the protein concentrations are measured by densitometry (Quantity one, Biorad) and BCA assay (bicinchoninic acid and copper sulfate, Sigma).

Purified natural wild-type INFα-7, D72N mutated INFα-7, V106L mutated INFα-7, or K159Q mutated INFα-7 proteins obtained according to this protocol, eventually scaled-up to produce higher amount of proteins, are used for the functional tests described below.

EXAMPLE 4

Evaluation of the Capacity of Wild-type and D72N Mutated IFNα-7 to Activate Signal Transduction The interferons are known to act through signaling pathways involving the JAK (Janus Kinase) and the STAT (Signal Transducers and Activators of Transcription) proteins. The binding of interferon to its receptor induces phosphorylation of the JAK proteins which in turn activate by phosphorylation the STAT proteins. Activated STAT proteins translocate to the nucleus where they bind to interferon response elements on gene promoters, which stimulates transcription of the respective genes. To study the signaling pathways initiated by interferon, the reporter gene technique was used. The procedure is described below.

The use of a human cell line stably transfected with the luciferase reporter gene under the control of an interferon responsive chimeric promoter provides the basis for this in vitro assay. Thus, the luciferase activity detected reflects the ability of the IFNs to induce a signal at the nuclear level.

Using this reporter gene assay, the dose-response curves exhibited by D72N mutated IFNα-7, wild-type INFα-7, and wild-type INFα-2 are analyzed and the results are expressed in terms of international units referring to Intron A (commercial product corresponding to interferon alpha 2b) activity per mg of IFNα protein.

This assay gives the following results:
581 IU/mg for the D72N mutated IFNα-7
489 IU/mg for the wild-type IFNα-7
698 IU/mg for the wild-type INFα-2

These results indicate that the capacity of D72N mutated IFNα-7 to activate signal transduction is sensibly similar to that of wild-type IFNα-7 and to that of wild-type IFNα-2.

EXAMPLE 5

Evaluation of Immunomodulatory Activity of D72N Mutated IFNα-7

IFNs type I (IFN alpha and IFN beta) are able to modulate certain functions of the immune system. They have been demonstrated to increase the dendritic cells (DC) maturation: increase in the expression of MHC class I (HLA-ABC) and II (HLA-DR) molecules, increase in the expression of the molecules involved in the co-stimulation of the T-lymphocytes, CD80, CD86 and CD83 molecules and increase in the stimulating function of T-lymphocytes.

a) Effect of D72N Mutated IFNα-7 on Dendritic Cell Maturation

Immunomodulatory activity of D72N mutated IFNα-7 was first investigated on dendritic cells maturation and compared to that of wild-type IFNα-2 chosen as a representative of commercial Intron A product.

To do so, dendritic cells were first generated from adult peripheral blood monocytes cultivated in the presence of GM-CSF and IL-4 cytokines. After purification using a CD14+ cells purification kit, these dendritic cells were placed in presence of 100 ng/mL of D72N mutated IFNα-7, or wild-type IFNα-2, and their phenotype was determined by FACS analysis aiming at looking for the expression of the MHC class I and II molecules and the CD40, CD80, CD86, CD83 and CD1α markers. The maturation state of these dendritic cells has also been compared to that obtained without IFNα treatment to provide a control with non-stimulated dendritic cells and to that obtained with 1 μg/ml LPS or 2.5 ng/ml TNFα, which are known to induce dendritic cell maturation.

The median value of the measures of fluorescence intensity for each marker and for the five experimental conditions, expressed as arbitrary unit, are presented in the following table:

TABLE 13

|  | HLA ABC | HLA DR | CD40 | CD80 | CD86 | CD83 | CD1a |
|---|---|---|---|---|---|---|---|
| No IFNα | 64 | 133 | 24 | 25 | 14 | 15 | 26 |
| LPS | 188 | 325 | 567 | 151 | 67 | 17 | 126 |
| TNFα | 72 | 209 | 355 | 49 | 9 | 13 | 181 |
| D72N IFNα-7 | 62 | 172 | 200 | 40 | 16 | 7 | 153 |
| Wild-type IFNα-2 | 87 | 281 | 331 | 76 | 45 | 15 | 155 |

The results of this test demonstrate that D72N mutated IFNα-7 protein possesses a weak capacity to stimulate dendritic cell maturation. In particular, in comparison to wild-type IFNα-2, the D72N mutated IFNα-7 protein shows an immunosuppressive activity.

b) Effect of D72N Mutated IFNα-7 on Cytokine Release by T-lymphocytes

Immunomodulatory activity of D72N mutated INFα-7 was also investigated by measuring cytokine release by T lymphocytes placed in presence of the mutated IFNα-7 protein and with or without a strong antigen (SEB) in order to mimic an immune response against an aggression. This test was also performed in presence of wild-type IFNα-2 used as control and chosen as representative of the Intron A commercial product.

To do so, peripheral blood mononuclear cells (PBMC) were isolated from healthy donors and stimulated for 16 hours in an appropriate medium containing anti-CD3 and anti-CD28 antibodies or SEB. In each culture was added 4 μug/mL of D72N mutated INFα-7 or wild-type IFNα-2. After stimulation, T lymphocytes were extracellularly labelled with anti-CD3, anti-CD4 and anti-CD69 antibodies or anti-CD3, anti-CD8 and anti-CD69 antibodies, and intracellularly labelled with specific antibodies directed against Th1-type cytokines (IFN-gamma) or Th2-type cytokines (IL-10). Fluorescent cells were analysed using FACSCALIBUR™ (an analytical flow cytometer) and CELLQUEST™ software (software for acquiring and analyzing data from flow cytometer).

The results obtained indicate that D72N mutated INFα-7 and wild-type IFNα-2 do not stimulate IL-10 and IFN-gamma release and, thus, do not activate T lymphocytes in absence of SEB. In contrast, D72N mutated IFNα-7 and wild-type IFNα-2 proteins stimulate cytokines (IL-10 and IFN-gamma) release by SEB-activated T-lymphocytes as shown in the table below. This table represents the cytokine release by T-lymphocytes in presence of SEB, expressed as percentage of the CD4+ CD69+ cells or CD8+ CD69+ cells for the CD4+ T-lymphocytes and CD8+ T-lymphocytes, respectively, and the percentage of CD69+ cells on total cells.

TABLE 14

| T-lymphocytes | | IFN gamma | IL-10 | CD69+ cells/total |
|---|---|---|---|---|
| CD4+ CD69+ | No IFNα | 11.9 | 7.5 | 1.26 |
| | D72N IFNα-7 | 38.54 | 24.16 | 2.37 |
| | Wild-type IFNα-2 | 19.6 | 24.68 | 2.7 |
| | No IFNα | 8.73 | 0.65 | 4.69 |

TABLE 14-continued

| T-lymphocytes | | IFN gamma | IL-10 | CD69+ cells/total |
|---|---|---|---|---|
| CD8+ CD69+ | D72N IFNα-7 | 35.91 | 6.06 | 7.97 |
| | Wild-type IFNα-2 | 16.37 | 4.26 | 10.02 |

These results clearly demonstrate that D72N mutated INFα-7 has a high capacity to stimulate cytokine release (IFN gamma and IL-10) by CD4+ T-lymphocytes and CD8+ T-lymphocytes previously activated by SEB antigen. In particular, the interferon gamma production by CD4+ or CD8+ T-lymphocytes is higher in presence of D72N mutated IFNα-7 than in presence of wild-type IFNα-2.

c) Effect of D72N Mutated INFα-7 on Cytokine Release by Monocytes

Finally, immunomodulatory activity of D72N mutated INFα-7 was investigated by measuring cytokine release by monocytes in absence or in presence of a bacterial toxic agent (LPS). This test was also performed in presence of wild-type IFNα-2 used as control and chosen as representative of the Intron A commercial product.

To do so, human peripheral blood mononuclear cells (PBMC) were isolated from healthy donors and their phenotype was analyzed to determine the relative amount of CD64+ CD4dim cells (CD64 and CD4dim are markers for blood monocytes). After an over-night culture, these PBMC were incubated in the culture medium alone (not stimulated cells) or in presence of LPS (stimulated cells). In each culture, 4 μg/mL of D72N mutated INFα-7 or wild-type IFNα-2 was added. After culture, cells were extracellularly labelled with anti-CD64 and anti-CD4dim, and intracellularly labelled with specific antibodies directed against Th1-type cytokines (TNF-alpha), IL-12 and IL-10.

Fluorescent cells were analyzed using FACSCALIBUR™ (an analytical flow cytometer) and CELLQUEST™ software (software for acquiring and analyzing data from flow cytometer).

The results obtained indicate that D72N mutated IFNα-7 protein and wild-type IFNα-2 do not stimulate cytokines (IL-10, IL-12 and TNF-alpha) release in absence of LPS.

In contrast, in presence of LPS, monocytes release cytokines (IL-10, IL-12 and TNF-α), this release being additionally increased in presence of D72N mutated IFNα-7 protein or wild-type INFα-2 as shown in the table below. This table represents cytokine release by monocytes in presence of LPS, expressed as percentage of the CD64+ CD4dim cells, and the percentage of CD4dim CD64+ cells on total cells.

TABLE 15

| | IL-10 | IL-12 | TNF-α | CD4dim CD64+ cells/total |
|---|---|---|---|---|
| No IFNα | 16.21 | 8.52 | 13.88 | 3.1 |
| D72N IFNα-7 | 57.4 | 27.31 | 54.92 | 3.43 |
| Wild-type IFNα-2 | 49.34 | 34.48 | 50.87 | 2.71 |

These results demonstrate that, in presence of LPS, D72N mutated IFNα-7 protein is able to stimulate cytokine release by monocytes. In particular, stimulation of IL-10 and TNF-α release by monocytes is higher in presence of D72N mutated IFNα-7 than in presence of wild-type IFNα-2.

EXAMPLE 6

Evaluation of In Vitro Antiproliferative Activity of D72N Mutated INFα-7 a) On the Human Lymphoblasts of Daudi Burkitt's Cell Line

These tests are carried out on four different types of IFNα-7, namely: wild-type IFNα-7, D72N mutated IFNα-7, V106L mutated INFα-7, and K159Q mutated INFα-7. Cells (human Daudi Burkitt's lymphoma cell line, hereinafter called "Daudi cells") cultivated beforehand in a RPMI 1640 medium (supplemented with 10% fetal calf serum and 2 mM of L-Glutamine) are inoculated in 96-well plates at the cellular density of $4.10^4$ cells/well.

In each well, Daudi cells are placed in contact of increasing concentrations of either natural wild-type IFNα-7, D72N mutated INFα-7, V106L mutated INFα-7, or K159Q mutated IFNα-7 mutated IFNα-7, ranging from 0.003 pM to 600 nM.

The Daudi cells are then incubated for 66 h at 37° C. under 5% $CO_2$ after which the Uptiblue reagent (Uptima) is added to the cultures. The rate of cell proliferation is quantified by measuring the fluorescence emitted at 590 nm (excitation 560 nm) after an additional period of incubation of 4 hours.

The antiproliferative activity of the mutated IFNα-7 proteins or wild-type IFNα-7 is based on the measurements of the IC50 corresponding to the concentration of INFα-7 inhibiting 50% of the cell growth.

At least 3 experiments, repeated 3 times were carried out for both proteins and for each concentration.

The average IC50 values measured for each of the tested IFNα-7 proteins appear in the tables below, as well as the average ratio corresponding to the IC50 value measured with the mutant protein over the IC50 value measured with the wild-type protein.

Results obtained with proteins purified by ion exchange chromatography:

TABLE 16

| | IC50 (pM) | mutant/wild-type ratio (standard deviation) |
|---|---|---|
| Wild-type IFNα-7 | 4.90 | — |
| V106L mutated IFNα-7 | 3.46 | 0.70 (0.37) |
| K159Q mutated IFNα-7 | 2.30 | 0.40 (0.20) |

Results obtained with proteins purified using blue cibacron:

TABLE 17

| | IC50 (pM) | wild-type/mutant ratio (standard deviation) |
|---|---|---|
| Wild-type IFNα-7 | 2.40 | — |
| D72N mutated IFNα-7 | 1.10 | 0.47 (0.17) |

This test demonstrates that the three mutated IFNα-7 proteins inhibit Daudi cells proliferation. Moreover, the cellular antiproliferative activity is slightly increased in the case of D72N mutated IFNα-7 and K159Q mutated IFNα-7 proteins by comparison with wild-type IFNα-7.

b) On the TF-1 Erythroleukemia Cell Line

The effect of D72N mutated IFNα-7 was also evaluated on TF-1 erythroleukemia cell line. This test was also performed in presence of wild-type IFNα-2 used as control and chosen as representative of the Intron A commercial product.

To do so, TF-1 cells were placed in contact of increasing concentrations of D72N mutated IFNα-7 or wild-type IFNα-2 (0.001 to 1000 ng/mL) and the cell proliferation measured.

Figure 5:
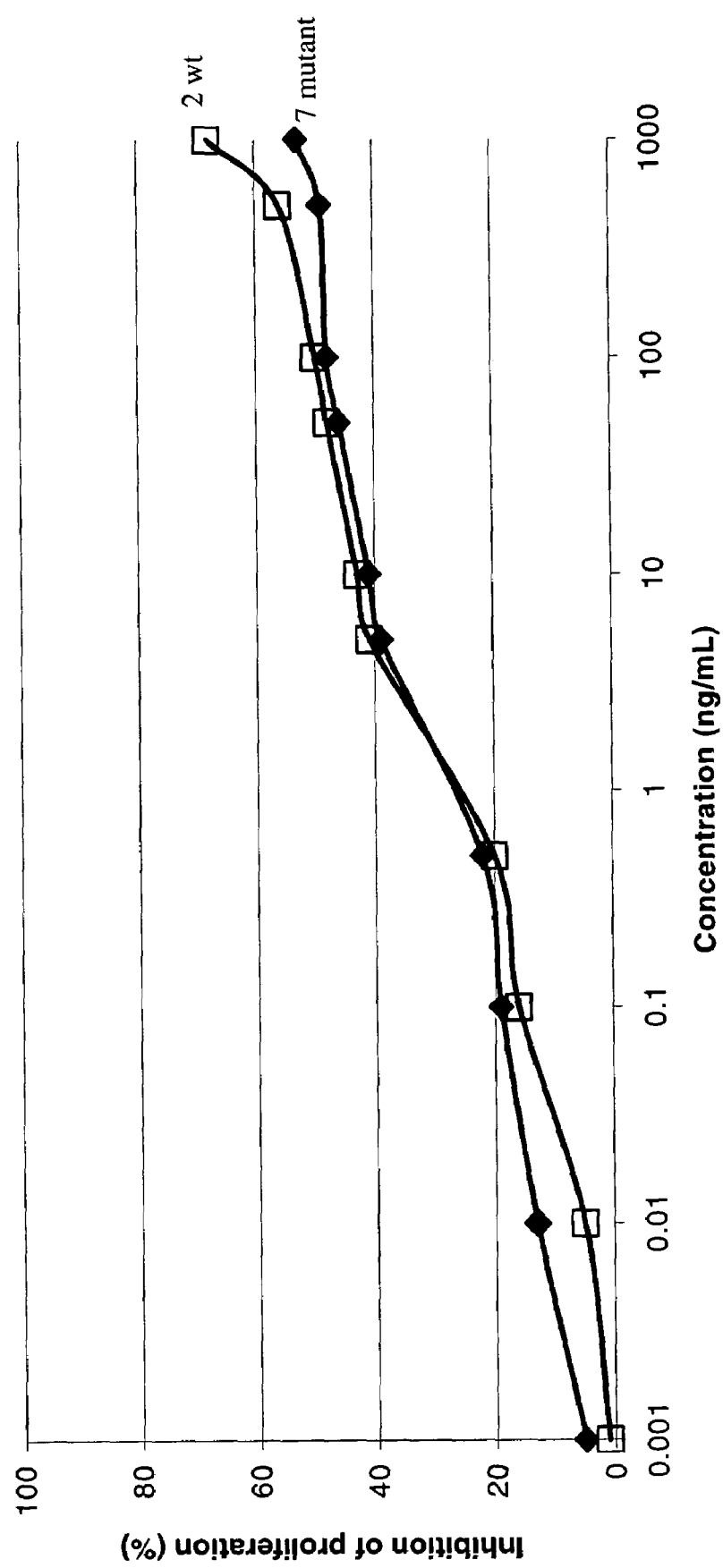

This experiment was repeated three times, and the results of one representative experiment are presented in FIG. 5.

These data indicate that D72N mutated IFNα-7 has a weak antiproliferative effect on TF-1 cells. In particular, the antiproliferative effect of D72N mutated IFNα-7 on TF-1 erythroleukemia cells is similar to that of wild-type IFNα-2.

EXAMPLE 7

Evaluation of the Antiviral Activity of D72N Mutated IFNα-7

The IFNs play an important role in the antiviral defence. The IFN antiviral activity is partly due to IFNs induced enzymatic systems, such as:

The 2'5' oligoadenylate synthetase, an enzyme which catalyzes the adenosine oligomere synthesis. These oligomeres activate the RNase L, an endoribonuclease which destroy the viral RNA once activated.

The Mx proteins (GTPases) which inhibit the synthesis and/or the maturation of viral transcripts. This activity is mainly exerted on the influenza virus.

The PKR protein (or p68 kinase) which is activated by the double-stranded RNA. The activated PKR inhibits protein synthesis.

The IFNs antiviral activity is also induced by other mechanisms such as, in the case of retroviruses, the inhibition of viral particles entry into the cells, the replication, the binding, the exit of the particles and the infective power of viral particles.

Finally, the IFNs exert an indirect antiviral activity by modulating certain functions of the immune system, in particular by favoring the response to cellular mediation (including an increase of the MHC class I and II molecules, increase of IL-12 and IFN-gamma production, increase of the CTL activities, among others).

The antiviral activity of D72N mutated INFα-7 has been evaluated both in vitro in cell culture and in vivo in mouse model. Both tests have been carried out in parallel with wild-type INFα-2 used as control and chosen as representative of the Intron A commercial product.

a) Antiviral Activity In Vitro in Cell Culture

This assay permits evaluation of the antiviral activity of D72N mutated INFα-7 in cell culture using the vesicular stomatitis virus (VSV), and comparison with that of wild-type INFα-2.

To do so, WISH human epithelial cells were cultivated for 24 hours in the presence of decreasing concentrations of D72N mutated INFα-7, or wild-type IFNα-2. Then, the cells were infected by the virus of vesicular stomatitis (VSV) during 24 to 48 additional hours and cell lysis was measured.

The antiviral activity of the different IFNα tested is determined by comparing the specific activity (IU/μg) corresponding to the amount of INFα-7 that inhibits 50% of cell lysis induced by the VSV. The unit IU/μg stands for international units referring to Intron A activity per μg of IFNα protein.

A similar experiment has been carried out three times, and the values of specific activity measured in one representative experiment are the following:

for D72N mutated INFα-7: 53 IU/μg for wild-type INFα-2: 330 IU/μg

The results of this experimentation indicate that D72N mutated INFα-7 protein possesses a weak antiviral activity in vitro in cell culture. In particular, in cell culture infected with VSV, the D72N mutated INFα-7 has a lower antiviral activity than the wild-type INFα-2.

b) Antiviral Activity In Vivo in Mouse Model

This test in vivo is performed in EMCV (Encephalomyocarditis virus) mouse model.

Human IFNs exhibit dose-dependent antiviral activity in the mouse which is in general 100 to 1,000 fold less than that exhibited by the same amount of mouse IFN (Meister et al. (1986). J. Gen. Virol. 67, 1633-1644).

Intraperitoneal injection of mice with Encephalomyocarditis virus (EMCV) gives rise to a rapidly progressive fatal disease characterized by central nervous system involvement and encephalitis (Finter N B (1973). Front Biol. 2: 295-360). Mouse and human interferon-alpha have both been shown to be effective in protecting mice against lethal EMCV infection (Tovey and Maury (1999). J. IFN Cytokine Res. 19: 145-155).

Groups of 20 six-week old Swiss mice were infected intraperitoneally with 100×$LD_{50}$ EMCV and treated one hour later, and then once daily for 3 days thereafter with 2 μg of D72N mutated IFNα-7 or wild-type IFNα-2 preparations. A control group was performed with animals having been treated with excipient only. The animals were followed daily for survival for 21 days.

Results are presented in FIG. 6 and indicate that the relative survival rate of the mice which have been treated with D72N mutated IFNα-7 is much higher than the survival rate of the non-treated mice, demonstrating the antiviral activity of D72N mutated IFNα-7 in vivo in mouse model. Moreover, after 14 days, 45% of the mice treated with D72N mutated INFα-7 are alive, while 30% of the mice treated with wild-type IFNα-2 are alive. Thus, the antiviral activity of D72N mutated IFNα-7 in vivo in mouse model is higher than that observed for the mice which have been treated with wild-type IFNα-2.

EXAMPLE 8

Evaluation of the Anti-tumoral Activity of D72N Mutated IFNα-7 in Mice Previously Inoculated with Malignant Friend Erythroleukemia Cells IFNα have been shown to be as effective in protecting mice against the growth of a clone of Friend leukemia cells resistant to the direct anti-proliferative activity of IFNα, as against IFN sensitive parental Friend leukemia cells (Belardelli et al., Int. J. Cancer, 30, 813-820, 1982; Belardelli et al., Int. J. Cancer, 30, 821-825, 1982), reflecting the importance of indirect immune mediated mechanisms in the anti-tumoral activity of IFNα.

The following experimentation permits evaluation of the anti-tumoral activity of D72N mutated INFα-7 in mice previously inoculated with Friend erythroleukemia cells, and comparison with that of wild-type IFNα-2 chosen as a representative of commercial Intron A product.

To do so, groups of 12 six-week old DBA/2 mice were inoculated intraperitoneally with 100,000 IFN resistant Friend leukemia cells (3C18) (20,000 $LD_{50}$) and treated one hour later and then once daily for 21 days thereafter with 2.0 μg of the wild-type INFα-2 or with 2.0 μg of D72N mutated IFNα-7 or an equivalent volume of excipient alone. The animals were then followed daily for survival and the primary efficacy analysis was the relative survival of each treatment group in comparison to its excipient only group.

The results of this experiment, presented in FIG. 7, indicate that, compared to mice which have not been treated with IFNα, treatment of mice with D72N mutated IFNα-7 results in an increase in the number of mice surviving after inoculation with highly malignant Friend erythroleukemia cells (FLC). After 45 days, 34% of the mice treated with D72N mutated INFα-7 are alive, while 50% of the mice treated with wild-type INFα-2 are alive. Thus, the survival rate of FLC inoculated mice is slightly lower after treatment with D72N mutated INFα-7 than after treatment with wild-type INFα-2.

All of these results demonstrate that D72N mutated INFα-7 possesses unique biological properties.

The invention claimed is:

1. An isolated polypeptide comprising:
   a) the amino acid sequence of SEQ ID NO. 2 or
   b) the amino acid sequence of amino acids 24 through 189 of SEQ ID NO. 2;
      wherein said sequence of (a) or (b) comprises a D95N SNP.

2. A composition comprising the polypeptide of claim 1 and at least one excipient.

3. The composition of claim 2, wherein said excipient is a pharmaceutically acceptable excipient.

4. The composition of claim 3, wherein said excipient is a buffer, aqueous vehicle, non-aqueous vehicle, wetting agent, dispersant, emulsifier, or preservative.

5. A pharmaceutical composition comprising the polypeptide of claim 1 and a pharmaceutically acceptable excipient.

6. The pharmaceutical composition of claim 5, wherein said excipient is a buffer, aqueous vehicle, non-aqueous vehicle, wetting agent, dispersant, emulsifier, or preservative.

7. An isolated polypeptide comprising an amino acid sequence at least 95% identical to
   a) the amino acid sequence of SEQ ID NO. 2 or
   b) the amino acid sequence of amino acids 24 through 189 of SEQ ID NO. 2;
      wherein said sequence of (a) or (b) comprises a D95N SNP and said polypeptide exhibits at least one antiviral, antiproliferative, or immunomodulatory activity.

8. The polypeptide of claim 7, wherein said amino acid sequence is at least 97% identical to the amino acid sequence SEQ ID NO: 2.

9. The polypeptide of claim 8, wherein said amino acid sequence is at least 99% identical to the amino acid sequence SEQ ID NO: 2.

10. The polypeptide of claim 7, wherein said amino acid sequence is at least 97% identical to the amino acid sequence of amino acids 24 through 189 of SEQ ID NO. 2.

11. The polypeptide of claim 7, wherein said amino acid sequence is at least 99% identical to the amino acid sequence of amino acids 24 through 189 of SEQ ID NO. 2.

12. A composition comprising the polypeptide of claim 7 and at least one excipient.

13. The composition of claim 12, wherein said excipient is a pharmaceutically acceptable excipient.

14. The composition of claim 13, wherein said excipient is a buffer, aqueous vehicle, non-aqueous vehicle, wetting agent, dispersant, emulsifier, or preservative.

15. A pharmaceutical composition comprising the polypeptide of claim 7 and a pharmaceutically acceptable excipient.

16. The pharmaceutical composition of claim 15, wherein said excipient is a buffer, aqueous vehicle, non-aqueous vehicle, wetting agent, dispersant, emulsifier, or preservative.

* * * * *

SEQUENCE LISTING

<160> NUMBER OF SEQ ID NOS: 20

<210> SEQ ID NO 1
<211> LENGTH: 1983
<212> TYPE: DNA
<213> ORGANISM: Homo sapiens

<400> SEQUENCE: 1

```
cacatcagta cttatgtcaa gtgctgaaaa gaaaaaagtg ttggcaatat ctggatgaat      60
actgcagcta gtgaagttta caaattattt tctcatataa agcaaaattc aaagcttcat     120
atactatgag aaaatttttt taaaattgat tcatatttct agcagttttg aatgattagg     180
tatgtaatta cattcatatt aatgtgtatt atacagattt ttattttgca tatgtaattt     240
gaaacaacaa aatttacatg aacaaattac attaaaagtt attccacaaa tatacttatc     300
taattaaact tagattttaa tagcttttaa acttagattt tagtttaact tttctgtcat     360
tcttaactta ctttgaataa aaagagcaaa cttcatactt tttatctgtg aagtagaggt     420
atatgtagaa tacctaaata gatatgccaa atctgtgtta ttaaaatttc atgaacattt     480
```

```
caattagaaa aaaataccat aaaaggcttt gagtgcaggg gaaaaacagg caatgatgaa    540
aaaaaaaatg aaaaacgtat ttaaacacat ggagagagtg cataaagaaa gcaaaaacag    600
agatagaaag taaaactagg gcatttagaa aatggaaatt agtatgttca ctatttaaga    660
cctatgcaca gagcaaagtc tccagaaaac ctagaggcca cggttcaagt tacccacctc    720
aggtagccta gtgatatttg caaaatccca atgcccggt cctttcttt actgatggtc      780
gtgctggtac tcagctacaa atccatctgc tctctgggct gtgatctgcc tcagacccac    840
agcctgcgta ataggagggc cttgatactc ctggcacaaa tgggaagaat ctctcctttc    900
tcctgcttga aggacagaca tgaattcaga ttcccgagg aggagtttga tggccaccag     960
ttccagaaga ctcaagccat ctctgtcctc catgagatga tccagcagac cttcaatctc   1020
ttcagcacag aggactcatc tgctgcttgg aacagagcc tcctagaaaa attttccact    1080
gaactttacc agcaactgaa tgacctggaa gcatgtgtga tacaggaggt tggggtggaa   1140
gagactcccc tgatgaatga ggacttcatc ctggctgtga ggaaatactt ccaaagaatc   1200
actctttatc taatggagaa gaaatacagc ccttgtgcct gggaggttgt cagagcagaa   1260
atcatgagat ccttctcttt ttcaacaaac ttgaaaaaag gattaaggag gaaggattga   1320
aaactggttc atcatggaaa tgattctcat tgactaatgc atcatctcac actttcatga   1380
gttcttccat ttcaaagact cacttctata accaccacaa gttgaatcaa aatttccaaa   1440
tgttttcagg agtgttaaga agcatcgtgt ttacctgtgc aggcactagt cctttacaga   1500
tgaccattct gatgtctcct ttcatctatt tatttaaata tttatttatt taactatttt   1560
tattatttaa attattttt atgtaatatc atatgtacct ttacattgtg gttaatgtaa    1620
caaatatgtt cttcatattt agccaatata ttaatttcct ttttcattaa attttttacta  1680
tacaaaattt cttgtgtttg tttatttttt aagattaaat gccaagcctg actgtataac   1740
ctgacttaaa aatagatgat ttaagtaagt tacctatcat aatttttattc aagttataga  1800
aaaatatatt tttctatacc aggttatctg ttgccttcat gatataaacg tgaacataaa   1860
aaatacagtt cttgttctct tgtatctttg attttttgtca ggaaagaaat ctaaaaacaa  1920
taataatgct gaattaatat cggttatact aactgctgta atgtgaggaa gtaaaaaaaa   1980
atg                                                                1983
```

<210> SEQ ID NO 2
<211> LENGTH: 189
<212> TYPE: PRT
<213> ORGANISM: Homo sapiens

<400> SEQUENCE: 2

```
Met Ala Arg Ser Phe Ser Leu Leu Met Val Val Leu Val Leu Ser Tyr
1               5                   10                  15

Lys Ser Ile Cys Ser Leu Gly Cys Asp Leu Pro Gln Thr His Ser Leu
            20                  25                  30

Arg Asn Arg Arg Ala Leu Ile Leu Leu Ala Gln Met Gly Arg Ile Ser
        35                  40                  45

Pro Phe Ser Cys Leu Lys Asp Arg His Glu Phe Arg Phe Pro Glu Glu
    50                  55                  60

Glu Phe Asp Gly His Gln Phe Gln Lys Thr Gln Ala Ile Ser Val Leu
65                  70                  75                  80

His Glu Met Ile Gln Gln Thr Phe Asn Leu Phe Ser Thr Glu Asp Ser
                85                  90                  95

Ser Ala Ala Trp Glu Gln Ser Leu Leu Glu Lys Phe Ser Thr Glu Leu
```

-continued

```
                100                 105                 110
Tyr Gln Gln Leu Asn Asp Leu Glu Ala Cys Val Ile Gln Glu Val Gly
        115                 120                 125

Val Glu Glu Thr Pro Leu Met Asn Glu Asp Phe Ile Leu Ala Val Arg
130                 135                 140

Lys Tyr Phe Gln Arg Ile Thr Leu Tyr Leu Met Glu Lys Lys Tyr Ser
145                 150                 155                 160

Pro Cys Ala Trp Glu Val Val Arg Ala Glu Ile Met Arg Ser Phe Ser
                165                 170                 175

Phe Ser Thr Asn Leu Lys Lys Gly Leu Arg Arg Lys Asp
        180                 185
```

<210> SEQ ID NO 3
<211> LENGTH: 18
<212> TYPE: DNA
<213> ORGANISM: Homo sapiens

<400> SEQUENCE: 3
tacccacctc aggtagcc                     18

<210> SEQ ID NO 4
<211> LENGTH: 21
<212> TYPE: DNA
<213> ORGANISM: Homo sapiens

<400> SEQUENCE: 4
catgaaagtg tgagatgatg c                 21

<210> SEQ ID NO 5
<211> LENGTH: 20
<212> TYPE: DNA
<213> ORGANISM: Homo sapiens

<400> SEQUENCE: 5
gtccttttct ttactgatgg                   20

<210> SEQ ID NO 6
<211> LENGTH: 20
<212> TYPE: DNA
<213> ORGANISM: Homo sapiens

<400> SEQUENCE: 6
tgtagctgag taccagcacg                   20

<210> SEQ ID NO 7
<211> LENGTH: 20
<212> TYPE: DNA
<213> ORGANISM: Homo sapiens

<400> SEQUENCE: 7
tcaatctctt cagcacagag                   20

<210> SEQ ID NO 8
<211> LENGTH: 20
<212> TYPE: DNA
<213> ORGANISM: Homo sapiens

<400> SEQUENCE: 8
ttcccaagca gcagatgagt                   20

<210> SEQ ID NO 9

-continued

```
<211> LENGTH: 20
<212> TYPE: DNA
<213> ORGANISM: Homo sapiens

<400> SEQUENCE: 9
tagaaaaatt ttccactgaa                                                20

<210> SEQ ID NO 10
<211> LENGTH: 20
<212> TYPE: DNA
<213> ORGANISM: Homo sapiens

<400> SEQUENCE: 10
gtcattcagt tgctggtaaa                                                20

<210> SEQ ID NO 11
<211> LENGTH: 20
<212> TYPE: DNA
<213> ORGANISM: Homo sapiens

<400> SEQUENCE: 11
gtgtgataca ggaggttggg                                                20

<210> SEQ ID NO 12
<211> LENGTH: 20
<212> TYPE: DNA
<213> ORGANISM: Homo sapiens

<400> SEQUENCE: 12
catcagggga gtctcttcca                                                20

<210> SEQ ID NO 13
<211> LENGTH: 20
<212> TYPE: DNA
<213> ORGANISM: Homo sapiens

<400> SEQUENCE: 13
tcccctgatg aatgaggact                                                20

<210> SEQ ID NO 14
<211> LENGTH: 20
<212> TYPE: DNA
<213> ORGANISM: Homo sapiens

<400> SEQUENCE: 14
atttcctcac agccaggatg                                                20

<210> SEQ ID NO 15
<211> LENGTH: 20
<212> TYPE: DNA
<213> ORGANISM: Homo sapiens

<400> SEQUENCE: 15
ggacttcatc ctggctgtga                                                20

<210> SEQ ID NO 16
<211> LENGTH: 20
<212> TYPE: DNA
<213> ORGANISM: Homo sapiens

<400> SEQUENCE: 16
tgattctttg gaagtatttc                                                20
```

```
<210> SEQ ID NO 17
<211> LENGTH: 20
<212> TYPE: DNA
<213> ORGANISM: Homo sapiens

<400> SEQUENCE: 17 tctcttttc aacaaacttg                                                    20

<210> SEQ ID NO 18
<211> LENGTH: 20
<212> TYPE: DNA
<213> ORGANISM: Homo sapiens

<400> SEQUENCE: 18
cttcctcctt aatcctttt                                                    20

<210> SEQ ID NO 19
<211> LENGTH: 21
<212> TYPE: DNA
<213> ORGANISM: Homo sapiens

<400> SEQUENCE: 19
tgtgatctgc ctcagaccca c                                                 21

<210> SEQ ID NO 20
<211> LENGTH: 26
<212> TYPE: DNA
<213> ORGANISM: Homo sapiens

<400> SEQUENCE: 20
tcaatccttc ctccttaatc cttttt                                            26
```